(12) United States Patent
Weston

(10) Patent No.: US 8,282,611 B2
(45) Date of Patent: Oct. 9, 2012

(54) REDUCED PRESSURE WOUND TREATMENT SYSTEM

(75) Inventor: Richard Scott Weston, Encinitas, CA (US)

(73) Assignee: BlueSky Medical Group, Inc., Memphis, TN (US)

(*) Notice: Subject to any disclaimer, the term of this patent is extended or adjusted under 35 U.S.C. 154(b) by 262 days.

(21) Appl. No.: 12/726,161

(22) Filed: Mar. 17, 2010

(65) Prior Publication Data

US 2010/0174251 A1 Jul. 8, 2010
US 2011/0087180 A2 Apr. 14, 2011

Related U.S. Application Data

(62) Division of application No. 11/098,203, filed on Apr. 4, 2005, now Pat. No. 7,708,724.

(60) Provisional application No. 60/559,727, filed on Apr. 5, 2004.

(51) Int. Cl.
*A61F 13/00* (2006.01)
(52) U.S. Cl. ......... 604/313; 604/304; 604/315; 604/543
(58) Field of Classification Search .................. 604/304, 604/313–315, 543
See application file for complete search history.

(56) References Cited

U.S. PATENT DOCUMENTS

| | | |
|---|---|---|
| 1,480,562 A | 1/1924 | Mock |
| 2,280,915 A | 4/1941 | Johnson |
| 2,568,933 A | 9/1951 | Robbins |
| 2,632,443 A | 3/1953 | Lesher |
| 2,682,873 A | 7/1954 | Evans et al. |
| 3,367,332 A | 2/1968 | Groves |

(Continued)

FOREIGN PATENT DOCUMENTS

CA 2198243 A1 2/1996

(Continued)

OTHER PUBLICATIONS

U.S. Appl. No. 11/064,813, filed Feb. 24, 2005 (published as 2005/0261642 A1) and its ongoing prosecution history, including without limitation Office Actions, Amendments, Remarks, and any other potentially relevant documents.

(Continued)

*Primary Examiner* — Lynne Anderson
(74) *Attorney, Agent, or Firm* — Knobbe, Martens, Olson & Bear LLP

(57) ABSTRACT

A reduced pressure treatment appliance is provided for treating a wound on the body of a patient. In some embodiments, the appliance comprises a cover, which can have a top cup member and an interface member. The interface member can have flow control means, configured to permit exudate from the wound to flow through the flow control means into the volume under the cover, but not in the opposite direction. Also, in some embodiments, the top cup member can have a lid member, a cup body member, and lid attachment means to removably attach the lid member to the cup body member. In some embodiments, the cover can be configured to facilitate access to the wound for monitoring, treatment and other purposes without removing the cover from the body. The wound treatment appliance can have a vacuum system to supply reduced pressure to the site of the wound in the volume under the cover. A suction bulb can he used lo provide a source of reduced pressure to the cover. Additionally, methods are provided for using various embodiments of the treatment appliance.

46 Claims, 4 Drawing Sheets

U.S. PATENT DOCUMENTS

| | | |
|---|---|---|
| 3,486,504 A | 12/1969 | Austin et al. |
| 3,572,340 A | 3/1971 | Lloyd et al. |
| 3,610,238 A | 10/1971 | Rich et al. |
| 3,874,387 A | 4/1975 | Barbieri |
| 3,993,080 A | 11/1976 | Loseff |
| RE29,319 E | 7/1977 | Nordby et al. |
| 4,112,947 A | 9/1978 | Nehring |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,250,882 A | 2/1981 | Adair |
| 4,316,466 A | 2/1982 | Babb |
| 4,382,441 A | 5/1983 | Svedman |
| 4,465,485 A | 8/1984 | Kashmer et al. |
| 4,468,227 A | 8/1984 | Jensen |
| 4,525,166 A | 6/1985 | Leclerc |
| 4,534,356 A | 8/1985 | Papadakis |
| 4,551,141 A | 11/1985 | McNeil |
| 4,573,965 A | 3/1986 | Russo |
| 4,655,766 A | 4/1987 | Theeuwes et al. |
| 4,710,165 A | 12/1987 | McNeil et al. |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,820,284 A | 4/1989 | Hauri |
| 4,921,488 A | 5/1990 | Maitz et al. |
| 4,936,834 A | 6/1990 | Beck et al. |
| 4,950,483 A | 8/1990 | Ksander et al. |
| 4,969,880 A | 11/1990 | Zamierowski |
| 4,972,829 A | 11/1990 | Knerr |
| 4,979,944 A | 12/1990 | Luzsicza |
| 5,055,198 A | 10/1991 | Shettigar |
| 5,056,510 A | 10/1991 | Gilman |
| 5,073,172 A | 12/1991 | Fell |
| 5,100,396 A | 3/1992 | Zamierowski |
| 5,149,331 A | 9/1992 | Ferdman et al. |
| 5,152,757 A | 10/1992 | Eriksson |
| 5,167,613 A | 12/1992 | Karami et al. |
| 5,176,663 A | 1/1993 | Svedman et al. |
| 5,261,893 A | 11/1993 | Zamierowski |
| 5,266,928 A | 11/1993 | Johnson |
| 5,279,608 A | 1/1994 | Cherif Cheikh |
| 5,328,614 A | 7/1994 | Matsumura |
| 5,358,494 A | 10/1994 | Svedman |
| 5,380,280 A | 1/1995 | Peterson |
| 5,437,651 A | 8/1995 | Todd et al. |
| 5,445,604 A | 8/1995 | Lang |
| 5,489,280 A | 2/1996 | Russell |
| 5,498,338 A | 3/1996 | Kruger et al. |
| 5,527,293 A | 6/1996 | Zamierowski |
| 5,549,584 A | 8/1996 | Gross |
| 5,562,107 A | 10/1996 | Lavender et al. |
| 5,636,643 A | 6/1997 | Argenta et al. |
| 5,643,189 A | 7/1997 | Masini |
| 5,645,081 A | 7/1997 | Argenta |
| 5,759,570 A | 6/1998 | Arnold |
| 5,785,688 A | 7/1998 | Joshi et al. |
| 5,830,496 A | 11/1998 | Freeman |
| 5,833,646 A | 11/1998 | Masini |
| 5,857,502 A | 1/1999 | Buchalter |
| 5,868,933 A | 2/1999 | Patrick et al. |
| 5,964,723 A | 10/1999 | Augustine |
| 6,071,267 A | 6/2000 | Zamierowski |
| 6,110,197 A | 8/2000 | Augustine et al. |
| 6,135,116 A | 10/2000 | Vogel et al. |
| D434,150 S | 11/2000 | Tumey |
| 6,142,982 A | 11/2000 | Hunt et al. |
| 6,168,800 B1 | 1/2001 | Dobos et al. |
| 6,176,307 B1 | 1/2001 | Danos et al. |
| 6,225,523 B1 | 5/2001 | Masini |
| 6,254,567 B1 | 7/2001 | Treu et al. |
| 6,255,552 B1 | 7/2001 | Cummings et al. |
| 6,287,521 B1 | 9/2001 | Quay et al. |
| 6,345,623 B1 | 2/2002 | Heaton et al. |
| 6,398,767 B1 | 6/2002 | Fleischmann |
| 6,402,724 B1 | 6/2002 | Smith et al. |
| 6,450,773 B1 | 9/2002 | Upton |
| 6,458,109 B1 | 10/2002 | Henley et al. |
| 6,465,708 B1 | 10/2002 | Augustine |
| 6,471,685 B1 | 10/2002 | Johnson |
| 6,471,982 B1 | 10/2002 | Lydon et al. |
| 6,482,491 B1 | 11/2002 | Samuelsen et al. |
| 6,491,684 B1 | 12/2002 | Joshi et al. |
| 6,553,998 B2 | 4/2003 | Heaton et al. |
| 6,599,262 B1 | 7/2003 | Masini |
| 6,648,862 B2 | 11/2003 | Watson |
| 6,673,028 B1 | 1/2004 | Argenta et al. |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,977,323 B1 | 12/2005 | Swenson |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,118,545 B2 | 10/2006 | Boyde |
| 7,128,735 B2 | 10/2006 | Weston |
| 7,195,624 B2 | 3/2007 | Lockwood |
| 7,216,651 B2 | 5/2007 | Argenta et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,494,482 B2 | 2/2009 | Orgill et al. |
| 7,524,315 B2 | 4/2009 | Blott et al. |
| 7,534,240 B1 | 5/2009 | Johnson |
| 7,534,927 B2 | 5/2009 | Lockwood |
| 7,569,742 B2 | 8/2009 | Haggstrom et al. |
| 7,611,500 B1 | 11/2009 | Lina et al. |
| 7,615,036 B2 | 11/2009 | Joshi et al. |
| 7,645,269 B2 | 1/2010 | Zamierowski |
| 7,699,830 B2 | 4/2010 | Martin |
| 7,708,724 B2 | 5/2010 | Weston |
| 7,753,894 B2 | 7/2010 | Blott et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,794,438 B2 | 9/2010 | Henley et al. |
| 7,815,616 B2 | 10/2010 | Boehringer et al. |
| 7,828,782 B2 | 11/2010 | Suzuki |
| 7,846,141 B2 | 12/2010 | Weston |
| 7,883,494 B2 | 2/2011 | Martin |
| 7,909,805 B2 | 3/2011 | Weston |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,062,272 B2 | 11/2011 | Weston |
| 8,062,273 B2 | 11/2011 | Weston |
| 8,080,702 B2 | 12/2011 | Blott et al. |
| 8,100,887 B2 | 1/2012 | Weston |
| 8,118,794 B2 | 2/2012 | Weston |
| 8,128,615 B2 | 3/2012 | Blott |
| 2001/0029956 A1 | 10/2001 | Argenta et al. |
| 2001/0034499 A1 | 10/2001 | Sessions et al. |
| 2002/0065494 A1 | 5/2002 | Lockwood et al. |
| 2002/0068913 A1 | 6/2002 | Fleischmann |

| | | |
|---|---|---|
| 2002/0115952 A1 | 8/2002 | Johnson et al. |
| 2002/0120185 A1 | 8/2002 | Johnson |
| 2002/0143286 A1 | 10/2002 | Turney |
| 2002/0150720 A1 | 10/2002 | Howard et al. |
| 2002/0161346 A1 | 10/2002 | Lockwood et al. |
| 2002/0183702 A1 | 12/2002 | Henley et al. |
| 2002/0198503 A1 | 12/2002 | Risk et al. |
| 2002/0198504 A1 | 12/2002 | Risk et al. |
| 2003/0014022 A1 | 1/2003 | Lockwood et al. |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0088202 A1 | 5/2003 | Gilman |
| 2003/0108587 A1 | 6/2003 | Orgill et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0208149 A1* | 11/2003 | Coffey .................. 602/48 |
| 2003/0212357 A1 | 11/2003 | Pace |
| 2003/0212431 A1 | 11/2003 | Brady et al. |
| 2003/0225347 A1 | 12/2003 | Argenta et al. |
| 2004/0019342 A1 | 1/2004 | Nagasuna et al. |
| 2004/0030304 A1 | 2/2004 | Hunt et al. |
| 2004/0039391 A1 | 2/2004 | Argenta et al. |
| 2004/0054338 A1 | 3/2004 | Bybordi et al. |
| 2004/0064132 A1 | 4/2004 | Boehringer et al. |
| 2004/0073151 A1 | 4/2004 | Weston |
| 2004/0122434 A1 | 6/2004 | Argenta et al. |
| 2004/0127834 A1 | 7/2004 | Sigurjonsson et al. |
| 2004/0127863 A1 | 7/2004 | Bubb et al. |
| 2004/0225208 A1 | 11/2004 | Johnson |
| 2004/0241214 A1 | 12/2004 | Kirkwood et al. |
| 2005/0004534 A1 | 1/2005 | Lockwood et al. |
| 2005/0010153 A1 | 1/2005 | Lockwood et al. |
| 2005/0028828 A1 | 2/2005 | Heaton et al. |
| 2005/0070835 A1 | 3/2005 | Joshi |
| 2005/0080372 A1 | 4/2005 | Nielsen et al. |
| 2005/0148913 A1 | 7/2005 | Weston |
| 2005/0203452 A1 | 9/2005 | Weston et al. |
| 2005/0222527 A1 | 10/2005 | Miller et al. |
| 2005/0222528 A1 | 10/2005 | Weston |
| 2005/0261615 A1 | 11/2005 | Weston |
| 2005/0261642 A1 | 11/2005 | Weston |
| 2005/0261643 A1 | 11/2005 | Bybordi et al. |
| 2006/0015087 A1 | 1/2006 | Risk, Jr. et al. |
| 2006/0025727 A1 | 2/2006 | Boehringer |
| 2006/0029650 A1 | 2/2006 | Coffey |
| 2006/0041247 A1 | 2/2006 | Petrosenko et al. |
| 2006/0100594 A1 | 5/2006 | Adams et al. |
| 2006/0116620 A1 | 6/2006 | Oyaski |
| 2006/0155260 A1 | 7/2006 | Blott et al. |
| 2007/0038172 A1 | 2/2007 | Zamierowski |
| 2007/0066945 A1 | 3/2007 | Martin |
| 2007/0129707 A1 | 6/2007 | Blott et al. |
| 2007/0141128 A1 | 6/2007 | Blott et al. |
| 2007/0265585 A1 | 11/2007 | Joshi et al. |
| 2007/0265586 A1 | 11/2007 | Joshi et al. |
| 2007/0293830 A1 | 12/2007 | Martin |
| 2008/0082059 A1 | 4/2008 | Fink et al. |
| 2008/0167593 A1 | 7/2008 | Fleischmann |
| 2008/0183119 A1 | 7/2008 | Joshi |
| 2008/0188820 A1 | 8/2008 | Joshi |
| 2008/0223378 A1 | 9/2008 | Henderson et al. |
| 2009/0012483 A1 | 1/2009 | Blott et al. |
| 2009/0054855 A1 | 2/2009 | Blott et al. |
| 2009/0069759 A1 | 3/2009 | Blott et al. |
| 2009/0131888 A1 | 5/2009 | Joshi |
| 2009/0192499 A1 | 7/2009 | Weston et al. |
| 2009/0204084 A1 | 8/2009 | Blott et al. |
| 2009/0216170 A1 | 8/2009 | Robinson et al. |
| 2009/0221977 A1 | 9/2009 | Blott et al. |
| 2009/0227969 A1 | 9/2009 | Jaeb et al. |
| 2009/0234309 A1 | 9/2009 | Vitaris et al. |
| 2009/0240185 A1 | 9/2009 | Jaeb et al. |
| 2009/0254054 A1 | 10/2009 | Blott et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0306580 A1 | 12/2009 | Blott et al. |
| 2009/0306609 A1 | 12/2009 | Blott et al. |
| 2009/0312723 A1 | 12/2009 | Blott et al. |
| 2009/0312728 A1 | 12/2009 | Randolph et al. |
| 2010/0036367 A1 | 2/2010 | Krohn |
| 2010/0069858 A1 | 3/2010 | Olson |
| 2010/0069863 A1 | 3/2010 | Olson |
| 2010/0100063 A1 | 4/2010 | Joshi et al. |
| 2010/0106114 A1 | 4/2010 | Weston et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0160879 A1 | 6/2010 | Weston |
| 2010/0160880 A1 | 6/2010 | Weston |
| 2010/0249733 A9 | 9/2010 | Blott et al. |
| 2010/0268198 A1 | 10/2010 | Buan et al. |
| 2010/0274207 A1 | 10/2010 | Weston |
| 2010/0286635 A1 | 11/2010 | Watson, Jr. |
| 2010/0298793 A1 | 11/2010 | Blott et al. |
| 2010/0305490 A1 | 12/2010 | Coulthard et al. |
| 2010/0324510 A1 | 12/2010 | Andresen et al. |
| 2010/0331797 A1 | 12/2010 | Patet et al. |
| 2011/0004172 A1 | 1/2011 | Eckstein et al. |
| 2011/0009835 A1 | 1/2011 | Blott |
| 2011/0009838 A1 | 1/2011 | Greener |
| 2011/0028918 A1 | 2/2011 | Hartwell |
| 2011/0034892 A1 | 2/2011 | Buan |
| 2011/0046584 A1 | 2/2011 | Haggstrom et al. |
| 2011/0046585 A1 | 2/2011 | Weston |
| 2011/0054421 A1 | 3/2011 | Hartwell |
| 2011/0054422 A1 | 3/2011 | Locke et al. |
| 2011/0054423 A1 | 3/2011 | Blott et al. |
| 2011/0087176 A2 | 4/2011 | Blott |
| 2011/0087178 A1 | 4/2011 | Weston |
| 2011/0092927 A1 | 4/2011 | Wilkes et al. |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0172615 A2 | 7/2011 | Greener |
| 2011/0230849 A1 | 9/2011 | Coulthard et al. |
| 2011/0251567 A1 | 10/2011 | Blott et al. |
| 2011/0282309 A1 | 11/2011 | Adie et al. |
| 2012/0041399 A1 | 2/2012 | Blott et al. |
| 2012/0053538 A1 | 3/2012 | Blott et al. |

FOREIGN PATENT DOCUMENTS

| | | |
|---|---|---|
| CA | 2367460 A1 | 10/2000 |
| CA | 2390513 A1 | 5/2001 |
| CA | 2121688 C | 7/2001 |
| CA | 2408305 A1 | 11/2001 |
| CA | 2458285 A1 | 3/2003 |
| CA | 2157772 C | 9/2003 |
| DE | 2809828 | 9/1978 |
| DE | 3935818 A1 | 5/1991 |
| DE | 40 12 232 A1 | 10/1991 |
| DE | 198 44 355 | 4/2000 |
| DE | 20 2005 019 670 U1 | 6/2006 |
| EP | 0020662 B1 | 7/1984 |
| EP | 0355186 A | 2/1990 |
| EP | 0777504 B1 | 10/1998 |
| EP | 0782421 B1 | 7/1999 |
| EP | 0708620 B1 | 5/2003 |
| EP | 1088569 B1 | 8/2003 |
| EP | 1440667 B1 | 3/2006 |
| EP | 1284777 B1 | 4/2006 |
| EP | 1171065 B1 | 3/2007 |
| EP | 1476217 B1 | 3/2008 |
| EP | 1121163 B1 | 11/2008 |
| EP | 2 098 257 A1 | 9/2009 |
| FR | 1 163 907 | 10/1958 |
| GB | 114754 | 4/1918 |
| GB | 641061 | 8/1950 |
| GB | 1 224 009 A | 3/1971 |
| GB | 1549756 A | 8/1979 |

| | | |
|---|---|---|
| GB | 2195255 A | 4/1988 |
| GB | 2378392 A | 2/2003 |
| JP | 2003-165843 | 6/2003 |
| SU | 1251912 A1 | 8/1986 |
| WO | WO 84/01904 | 5/1984 |
| WO | WO 90/11795 | 10/1990 |
| WO | WO 91/00718 | 1/1991 |
| WO | WO 92/20299 | 11/1992 |
| WO | WO 96/05873 | 2/1996 |
| WO | WO 99/01173 | 1/1999 |
| WO | WO 00/07653 | 2/2000 |
| WO | WO 00/50143 A | 8/2000 |
| WO | WO 00/59424 | 10/2000 |
| WO | WO 01/19430 A1 | 3/2001 |
| WO | WO 01/34223 | 5/2001 |
| WO | WO 01/85248 | 11/2001 |
| WO | WO 01/93793 A | 12/2001 |
| WO | WO 02/083046 A1 | 10/2002 |
| WO | WO 02/092783 | 11/2002 |
| WO | WO 03/092620 | 11/2003 |
| WO | WO 2004/024300 | 3/2004 |
| WO | WO 2004/037334 | 5/2004 |
| WO | WO 2005/025666 | 3/2005 |
| WO | WO 2005/051461 | 6/2005 |
| WO | WO 2005/070480 | 8/2005 |
| WO | WO 2005/082435 | 9/2005 |

OTHER PUBLICATIONS

U.S. Appl. No. 12/719,767, filed Mar. 8, 2010, including its ongoing prosecution history, including without limitation Office Actions, Amendments, Remarks, and any other potentially relevant documents.

U.S. Appl. No. 12/719,715, filed Mar. 8, 2010, including its ongoing prosecution history, including without limitation Office Actions, Amendments, Remarks, and any other potentially relevant documents.

U.S. Appl. No. 12/848,817, filed Aug. 2, 2010 and its ongoing prosecution history, including without limitation Office Actions, Amendments, Remarks, and any other potentially relevant documents.

U.S. Appl. No. 12/744,055, filed May 20, 2010, including its ongoing prosecution history, including without limitation Office Actions, Amendments, Remarks, and any other potentially relevant documents.

U.S. Appl. No. 12/744,277, filed Sep. 20, 2010, including its ongoing prosecution history, including without limitation Office Actions, Amendments, Remarks, and any other potentially relevant documents.

U.S. Appl. No. 12/938,291, filed Nov. 2, 2010, including its ongoing prosecution history, including without limitation Office Actions, Amendments, Remarks, and any other potentially relevant documents.

U.S. Appl. No. 12/940,788, filed Nov. 5, 2010, and its ongoing prosecution history, including without limitation Office Actions, Amendments, Remarks, and any other potentially relevant documents.

U.S. Appl. No. 12/744,218, filed Sep. 20, 2010, including its ongoing prosecution history, including without limitation Office Actions, Amendments, Remarks, and any other potentially relevant documents.

U.S. Appl. No. 60/559,727, filed Apr. 5, 2004, Weston.

U.S. Appl. No. 60/573,655, filed May 21, 2004, Weston.

U.S. Appl. No. 12/941,390, filed Nov. 8, 2010, including its ongoing prosecution history, including without limitation Office Actions, Amendments, Remarks, and any other potentially relevant documents), Weston.

Achterberg et al., "Hydroactive dressings and serum proteins: an in vitro study," Journal of Wound Care, vol. 5, No. 2, Feb. 1996.

Argenta, Louis C., et al., "Vacuum-Assisted Closure: A New Method for Wound Control and Treatment; Clinical Experience", Ann Plas Surg 1997;38:563-577 (Dec. 10, 1996).

Aubrey, D.A., et al., Treatment of the Perineal Wound after Proctectomy by Intermittent Irrigation, Arch. Surg., Oct. 1984, 119, pp. 1141-1144.

Bagautdinov, N.A. "Variant of External Vacuum Aspiration in the Treatment of Purulent Diseases of Soft Tissues," in Current Problems in Modern Clinical Surgery: Interdepartmental Collection, edited by V.Ye. Volkov et al. (Chuvashia State University, Cheboksary, USSR 1986) pp. 94-96.

Biblehimer, Helen L., "Dealing With a Wound that Drains 1.5 Liters a Day," RN, Aug. 1986, pp. 21-23, USA.

Bier, A., Hyperemia as a Therapeutic Agent, Ed. Dr. Gustavus M. Blech, *A. Robertson & Co* ., Chicago 1905, pp. 74-85.

Brubacher, "To Heal A Draining Wound", RN Mar. 1982, 7 pages.

Bucalo et al. "Inhibition of Cell Proliferation by Chronic Wound Fluid." Wound Repair and Regeneration, Miami, 1993, pp. 181-186.

Chariker, M.E., et al, Effective Management of Incisional and Cutaneous Fistulae with Closed Suction Wound Drainage, Contemporary Surgery. Jun. 1989, vol. 34 USA, pp. 59-63.

Chintamani, et al., "Half versus full vacuum suction drainage after modified radical mastectomy for breast cancer—a prospective randomized clinical trial", Research Article (Jan. 27, 2005), 1-5.

Costunchenok, BM, Effect of Vacuum on Surgical Purulent Wounds, Vestnik Chirurgia, 1986, 6 pages.

Davydov et al. "Pathogenic Mechanism of the Effect of Vacuum Therapy on the Course of the Wound Process" pp. 43-46 (Dec. 1990).

Davydov, Y., "Bacteriological and cytological evaluation of the vacuum therapy of suppurative wounds," Vestnik Khirurgii, Oct. 1988, pp. 48-52.

Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.

Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.

De Lange, M.Y., et al., "Vacuum-Assisted Closure: Indications and Clinical Experience", Eur J Plast Surg (2000) 2;178-182 (Feb. 9, 2000).

Dilmaghani et al., A Method for Closed Irrigation and Suction Therapy in Deep Wound Infections, Journal of Bone and Joint Surgery, 1969, vol. 51-A, No. 2, pp. 323-342.

Fleischmann, Vacuum sealing: indication, technique, and results, European Journal of Orthopaedic Surgery & Traumatology (1995), pp. 37-40.

Fleischmann, W. Wund Forum Spezial. IHW '94. "Vakuumversiegelung zur Behandlung von Problemwuden" (with English translation: Vacuum Sealing for Treatment of Problematical Wounds).

Garcia-Rinaldi, R., et al., Improving the Efficiency of Wound Drainage Catheters, Amer. Journ. of Surg., Sep. 1975, pp. 130, 372-373.

Hartz, R.S., et al., Healing of the Perineal Wound, Arch. Surg., Apr. 1980, 115, pp. 471-474.

Health Technology, Literature R., "Vacuum Assisted Closure Therapy for Wound Care", Health Technology Literature Review (Dec. 2004), 3-59.

International Preliminary Report on Patentability of International Application No. PCT/US05/17225 consisting of 6 pages, Jul. 31, 2006.

International Search Report of International Application No. PCT/NL2004/000565 consisting of 5 pages, Jul. 29, 2005.

International Search Report of International Application No. PCT/GB00/01566 consisting of 2 pages, Sep. 25, 2000.

International Search Report of International Application No. PCT/GB00/04278 consisting of 2 pages, Feb. 22, 2001.

International Search Report of International Application No. PCT/US05/17225 consisting of 1 page, Oct. 4, 2005.

International Search Report of International Application No. PCT/US2007/011278 consisting of 6 pages, May 11, 2006.

Jeter, K.F., et al, "Managing Draining Wounds and Fistulae: New and Established Methods", Chronic Wound Care, pp. 240-246.

Johnson, F.E., An Improved Technique for Skin Graft Placement using a Suction Drain, Surgery, Gynecology and Obstetrics, Dec. 1984, 3 pages.

KCI Inc., If It's Not VAC Therapy, It's Not Negative Pressure Wound Therapy, Jan. 2005.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Kremlin Papers, A Collection of Published Studies Complementing the Research and Innovation of Wound Care, from Vestnik Khirurgii, BlueSky Publishing, A Div. of BlueSky Medical Group Inc., 2004.
Landes, R.R. and I. Melnick, An Improved Suction Device for Draining Wounds, Arch. Surg., May 1972, 104, p. 707.
Linden, Willem van der, et al, "Randomized Trial of Drainage After Cholecystectomy: Suction Versus Static Drainage Through a Main Wound Versus a Stab Incision", American Journal of Surgery, Feb. 1981, vol. 141, pp. 289-294.
Mcfarlane, R.M., The Use of Continuous Suction under Skin Flaps, Br. Journ. Plast. Surg., pp. 77-86.
Mclaughlan, J, et al, "Sterile Microenvironment for Postoperative Wound Care", The Lancet, Sep. 2, 1978, pp. 503-504.
Meyer, W. and V. Schmeiden, Bier's Hyperemic Treatment, Published 1908 W. B. Saunders Company, pp. 44-65.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Nakayama, Y, et al, "A New Method for the Dressing of Free Skin Grafts", Plastic and Reconstructive Surgery, Dec. 1990 pp. 1216-1219, UK.
PCT International Search Report of PCT/US2007/011321, International Filing Date May 10, 2007.
Ramirez, O.M., et al., Optimal Wound Healing under Op-Site Dressing, Ideas and Innovations, 73(3), pp. 474-475.
Ranson, J. H. C., et al, "Safer Intraperitoneal Sump Drainage", Surgery, Gynecology & Obstetrics, Nov. 1973, vol. 137, pp. 841-842.
Sames, C.P., Sealing of Wounds with Vacuum Drainage, Br. Med. Journ., Nov. 5, 1977, p. 1223, Correspondence.
Solovev et al., "The Method of Treatment of Immature External Fistulas in the Upper Gastrointestinal Tract," USSR Ministry of Health, S.M. Kirov Gorky State Medical Institute, 1987.
Stewart, Joanne, "Next generation products for wound management," http://www.worldwidewounds.com/2003/april/Stewart/Next-Generation-Products.html, Nov. 2002.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., A Dressing System Providing Fluid Supply and Suction Drainage Used for Continuous or Intermittent irrigation, Annals of Plastic Surgery, vol. 17, No. 2, Aug. 1986, pp. 125-133.
Svedman, P., Irrigation Treatment in Split-Thickness Skin Grafting of Intractable Leg Ulcers, Scand J. Plast. Reconst. Surg., 1985, 19, pp. 211-213.
Svedman, P., Irrigation Treatment of Leg Ulcers, The Lancet, Sep. 1983, pp. 532-534.
Swift, et al, Quorum Sensing in *Aeromonas hydrophila* and *Aeromonas salmoncida* : Identification of LuxRI Homologs AhyRI and AsaRI and Their Cognate N-Acylhomoserine Lactone Signal Molecules, J. Bacteriol., 1997, 179(17):5271-5281.
Teder and Svedman et al., Continuous Wound Irrigation in the Pig, Journal of Investigative Surgery, 1990, vol. 3, pp. 399-407.
Tribble, David E. M.D., An Improved Sump Drain-Irrigation Device of Simple Construction, Archives of Surgery New York, 1972, vol. 105, pp. 511-513.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005), 185-194.
Vijanto, J. and J. Raekallio, Local Hyperalimentation of Open Wounds, Br. J. surg., 1976, 63, pp. 427-430.
Westaby, S., et al., A Wound Irrigation Device, The Lancet, Sep. 2, 1978, pp. 503-504.
Wooding-Scott, Margaret, et al., No Wound is Too Big for Resourceful Nurses, RN, USA, Dec. 1988, pp. 22-25.
Written Opinion of the International Search Report of PCT/US2007/011278 consisting of 7 pages, Dec. 11, 2007.
Written Opinion of the International Searching Authority of PCT International Search Report of PCT/US2007/011321, International Filing Date May 10, 2007.
Wu, W.S., et al. Vacuum therapy as an intermediate phase in would closure: a clinical experience, Eur J Plast Surg (2000) 23: pp. 174-177.
U.S. Appl. No. 13/302,175, filed Nov. 22, 2011, including its ongoing prosecution history, including without limitation Office Actions, Amendments, Remarks, and any other potentially relevant documents, Weston.
U.S. Appl. No. 13/302,980, filed Nov. 22, 2011, including its ongoing prosecution history, including without limitation Office Actions, Amendments, Remarks, and any other potentially relevant documents, Blott et al.
U.S. Appl. No. 12/419,542, filed Apr. 7, 2009, Including its ongoing prosecution history, including without limitation Office Actions, Amendments, Remarks, and any other potentially relevant documents.
U.S. Appl. No. 12/719,715, filed Mar. 3, 2010, including its ongoing prosecution history, including without limitation Office Actions, Amendments, Remarks, and any other potentially relevant documents.
U.S. Appl. No. 12/832,031, filed Jul. 7, 2010 (published as 2010/0274207 A1) and its ongoing prosecution history, including without limitation Office Actions, Amendments, Remarks, and any other potentially relevant documents.
U.S. Appl. No. 12/832,032, filed Jul. 7, 2010, and its ongoing prosecution history, including without limitation Office Actions, Amendments, Remarks, and any other potentially relevant documents.
U.S. Appl. No. 12/416,829, filed Apr. 1, 2009, including its ongoing prosecution history, including without limitation Office Actions, Amendments, Remarks, and any other potentially relevant documents.
U.S. Appl. No. 12/744,055, filed May 20, 2010, and its ongoing prosecution history, including without limitation Office Actions, Amendments, Remarks, and any other potentially relevant documents.
U.S. Appl. No. 12/981,337, filed Dec. 29, 2010, including its ongoing prosecution history, incuding without limitation Office Actions, Amendments, Remarks, and any other potentially relevant documents.
U.S. Appl. No. 13/092,042, filed Apr. 21, 2011, including its ongoing prosecution history, including without limitation Office Actions Amendments (including Preliminary Communication filed Nov. 8, 2010), Remarks, and any other potentially relevant documents.
U.S. Appl. No. 13/212,039, filed Aug. 17, 2011, and its ongoing prosecution history, including without limitation Office Actions, Amendments, Remarks, and any other potentially relevant documents.
U.S. Appl. No. 13/217,074, filed Aug. 24, 2011, and its ongoing prosecution history, including without limitation Office Actions, Amendments, Remarks, and any other potentially relevant documents.
Meyer, W. & Schmieden, V., Bier's Hyperemic Treatment, W B. Saunders Company 1908, (the entire reference has been submitted, but pp. 44-65 may be the most relevant).
Solovev, V.A. "Treatment and Prevention of Suture Failures after Gastric Resection" (Dissertation Abstract) (S.M. Kirov Gorky State Medical Institute, Gorky USSR 1988).
Webb, New Techniques in Wound Management: Vacuum-Assisted Wound Closure, Journal of the American Academy of Orthopaedic Surgeons, v. 10, No. 5, pp. 303-311, Sep. 2002.
Webster's Revised Unabridged Dictionary, published 1913 by C. & G. Merriam Co., definition of Flapper Valve, downloaded from Free Online Dictionary.

Vijanto, J. and J. Raekallio, Local Hyperalimentation of Open Wounds, *Br. J. Surg.*, 1976, 63, 427-430.

Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.

International Search Report, International Application No. PCT/US2005/17225, dated Oct. 4, 2005, in 1 page.

* cited by examiner

REDUCED PRESSURE WOUND TREATMENT SYSTEM

CROSS-REFERENCE TO RELATED APPLICATIONS

This application is a divisional of U.S. application Ser. No. 11/098,203, filed on Apr. 4, 2005, which claims the benefit of U.S. Provisional Application No. 60/559,727, filed on Apr. 5, 2004. The full disclosures of U.S. application Ser. No. 11/098,203 and U.S. Provisional Application No. 60/559,727 are hereby incorporated by reference as if fully set forth herein.

BACKGROUND OF THE INVENTION

1. Field of the Invention

The present invention generally relates to treatment of wounds, and more specifically to improved apparatus and methods for treating a wound on a patient's body by applying reduced pressure to the body at the site of the wound. In this context, the term "wound" is to be interpreted broadly, to include any wound that may be treated using reduced pressure.

2. Description of the Related Art

The treatment of open or chronic wounds that are too large to spontaneously close or otherwise fail to heal by means of applying reduced pressure to the site of the wound is well known in the art. One such system is disclosed in U.S. patent application Ser. No. 10/652,100, which was filed with the U.S. Patent and Trademark Office on Aug. 28, 2003. The disclosure of this U.S. patent application is incorporated herein by reference. Another system is disclosed in U.S. patent application Ser. No. 11/026,733, entitled "Improved Reduced Pressure Wound Treatment Appliance," which was filed with the U.S. Patent and Trademark Office on Dec. 30, 2004. The disclosure of this U.S. patent application is also incorporated herein by reference. Yet another system is disclosed in U.S. patent application Ser. No. 11/064,813, entitled "Improved Flexible Reduced Pressure Wound Treatment Appliance," which was filed with the U.S. Patent and Trademark Office on Feb. 24, 2005. The disclosure of this U.S. patent application is also incorporated herein by reference.

Reduced pressure wound treatment systems currently known in the art commonly involve placing a treatment device that is impermeable to liquids over the wound, using various means to seal the treatment device to the tissue of the patient surrounding the wound, and connecting a source of reduced pressure (such as a vacuum pump) to the treatment device in a manner so that an area of reduced pressure is created under the treatment device in the area of the wound. The systems also typically act to remove exudate that may be aspirated from the wound. Thus, such systems also typically have a separate collection device located between the reduced pressure source and the treatment device to collect. This collection device represents a separate source of expense in reduced pressure wound treatment. In addition, it is advantageous in some circumstances to remove exudate from the wound so that the exudate does not remain in the presence of the wound. For example, healing of the wound may be enhanced by the removal of exudate from the wound in some circumstances. In yet other cases, it may be advantageous to be able to gain physical access to the wound without having to remove the treatment device from the body surrounding the wound. For example, it may be desirable to monitor or treat the condition of the wound during the treatment process. If the treatment device is sealed to the body using an adhesive tape, removing the adhesive tape to monitor or treat the wound may cause discomfort and pain for the patient.

Therefore, there is a need for a wound treatment device that can eliminate the requirement for a separate collection device to collect exudate from the wound. This type of device could reduce the expense involved in wound treatment by eliminating the need for the collection device. There is also a need for such a treatment device to remove exudate from the presence of the wound to aid in wound healing. It may also be desirable for this type of treatment device to be disposable in certain circumstances. Further, there is a need for a treatment device that would allow for physical access to the wound without the need for removing the treatment device from the body. This type of device could enhance patient comfort. In addition, where the access is simple and quickly obtained, it could also decrease the cost of wound treatment by reducing the time required of healthcare practitioners to be involved in wound treatment. Finally, there is also a need for a reduced pressure treatment system that is relatively inexpensive, while meeting the needs described above.

SUMMARY OF THE INVENTION

The present invention is directed to reduced pressure treatment appliances and methods that satisfy the needs described above. As described in greater detail below, they have many advantages over existing reduced pressure treatment apparatus and methods when used for their intended purpose, as well as novel features that result in new reduced pressure treatment appliances and methods that are not anticipated, rendered obvious, suggested, or even implied by any of the prior art apparatus or methods, either alone or in any combination thereof.

In accordance with the present invention, a treatment appliance is provided for treating a wound on a body by applying reduced pressure (i.e., pressure that is below ambient atmospheric pressure) to the wound in a controlled manner for a selected time period in a manner that overcomes the disadvantages of currently existing apparatus. For example, the application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

In one embodiment of a first version of the present invention, an appliance for treating a wound on a body is comprised of a cover, sealing means to seal the cover to the body, which are described in more detail below, and reduced pressure supply means, which are also described in more detail below. The cover, which is sized to be placed over and enclose the wound, is further comprised of a top cup member, an interface member, and interface attachment means for removably attaching the top cup member to the interface member. The interface member is further comprised of flow control means that permit exudate from the wound to flow from the wound into the top cup member, but not in the opposite direction. Thus, in this embodiment, the interface member is sealed to the body by the sealing means and exudate from the wound flows from the wound through the flow control means in the interface member into the volume of the cover above the interface member. The flow control means do not allow the exudate to flow back into the area of the wound under the interface member. The cover and the sealing means allow reduced pressure to be maintained in the volume under the cover at the site of the wound. The reduced pressure supply means operably connect the cover to a reduced pressure supply source that provides a supply of reduced pressure to the cover, so that the volume under the cover at the site of the wound is supplied with reduced pressure by the reduced pressure supply source.

In some embodiments of this first version of the present invention, the cover may be approximately cylindrical in shape. In other embodiments, the cover may be approximately cup-shaped. In some embodiments, the sealing means may be comprised of the suction of the interface member against the body, such suction being produced by the presence of reduced pressure in the volume under the cover at the site of the wound. In still other embodiments, the top cup member and the interface member are each comprised of materials from the group consisting of semi-rigid materials, rigid materials, and combinations of such materials. Further, in some embodiments, the interface member is further comprised of a membrane portion that is disposed approximately adjacent to the body and the flow control means is comprised of at least one one-way valve operably disposed in the membrane portion. In other embodiments, the interface member may be further comprised of a membrane portion that is disposed approximately adjacent to the body and that permits fluid to flow in only one direction, and the flow control means is comprised of all or a portion of the membrane. In some embodiments of this first version of the present invention, the interface attachment means may be comprised of an o-ring seal or a magnetic seal. In other embodiments, a portion of the interface member may be of a size and shape adapted to fit tightly against a portion of the top cup member, wherein an operable seal (described in more detail below) is created between the interface member and the top cup member. In yet other embodiments, the sealing means may be comprised of an adhesive that is disposed between a portion of the cover and the portion of the body adjacent to said portion of the cover. In still other embodiments, the sealing means may be comprised of an adhesive tape that is disposed over a portion of the cover and the portion of the body adjacent to said portion of the cover. In other embodiments, the top cup member is further comprised of a port and flow shutoff means operably connected to the port, wherein the flow shutoff means halt or inhibit the supply of reduced pressure to the cover when the level of exudate under the cover at the site of the wound reaches a predetermined level. In yet other embodiments, the interface attachment means does not provide for removal of the top cup member from the interface member.

In some embodiments of this first version of the present invention, the top cup member of the cover may be further comprised of a lid member, a cup body member, and lid attachment means to removably attach the lid member to the cup body member. In some of these embodiments, the cover is approximately cylindrical in shape. In other embodiments, the interface attachment means provides for removable attachment of the top cup member to the interface member, but does not provide for permanent attachment of the top cup member to the interface member. In some of these embodiments, the interface attachment means may be comprised of an o-ring seal or a magnetic seal. In other embodiments, a portion of the interface member may be of a size and shape adapted to fit tightly against a portion of the top cup member, wherein an operable seal is created between the interface member and the top cup member. In still other embodiments, the interface attachment means provides for permanent attachment of the top cup member to the interface member, but does not provide for removable attachment of the top cup member to the interface member. In yet other embodiments, the lid attachment means may be comprised of an o-ring seal or a magnetic seal. In other embodiments, a portion of the lid member is of a size and shape adapted to fit tightly against a portion of the cup body member, wherein an operable seal is created between the lid member and the cup body member.

In other embodiments of this first version of the present invention, the cover is comprised of a lid member, a cup body member, and lid attachment means to removably attach the lid member to the cup body member. In these embodiments, the cover is sized to be placed over and enclose the wound and adapted to maintain reduced pressure in the volume under the cover at the site of the wound. Also in these embodiments, the sealing means, which are described in more detail below, are used to seal the cup body member of the cover to the body so that reduced pressure may be maintained in the volume under the cover at the site of the wound. Reduced pressure supply means operably connect the cover to a reduced pressure supply source, which provides a supply of reduced pressure to the cover so that the volume under the cover at the site of the wound is supplied with reduced pressure by the reduced pressure supply source. In some of these embodiments, the lid attachment means may be comprised of an o-ring seal or a magnetic seal. In other embodiments, a portion of the lid member is of a size and shape adapted to fit tightly against a portion of the cup body member, wherein an operable seal is created between the lid member and the cup body member. In some of these embodiments, a portion of the lid member is approximately cylindrical in shape and a portion of the cup body member is approximately cylindrical in shape and said portions have threads and means to receive threads, so that when such portions are screwed together an operable seal is created between the lid member and the cup body member.

In a second version of the present invention, an appliance for administering reduced pressure treatment to a wound on a body is comprised of a treatment device and a vacuum system. In various embodiments of this second version of the invention, the treatment device is also comprised of a cover and sealing means, which may have substantially the same structure, features, characteristics and operation as the cover and sealing means, respectively, described above in connection with the first version of the present invention. In this second version of the invention, the vacuum system is further comprised of a reduced pressure supply source that provides a supply of reduced pressure and reduced pressure supply means (which are described in more detail below) to operably connect the treatment device to the reduced pressure supply source, so that the volume under the treatment device at the site of the wound is supplied with reduced pressure by the reduced pressure supply source. In various embodiments of this second version of the invention, the reduced pressure supply means may generally have substantially the same structure, features, characteristics and operation as the reduced pressure supply means described above in connection with the first version of the invention.

In some embodiments of this second version of the invention, the reduced pressure supply source is comprised of a vacuum pump. In some of these embodiments, the reduced pressure supply source further comprises a control system for the vacuum pump, wherein the control system may control at least the level of suction produced by the vacuum pump or the rate of fluid flow produced by the vacuum pump, or any combination of rate of suction and rate of fluid flow of the vacuum pump. In other embodiments, the reduced pressure supply source further comprises a filter operably positioned between the vacuum pump and the reduced pressure supply means. In these embodiments, the filter prevents the venting of and contamination of the vacuum pump by micro-organisms or fluids (or both) aspirated from the wound. In yet other embodiments, the vacuum pump is comprised of a portable vacuum pump. In still other embodiments of this second version of the invention, the reduced pressure supply means is comprised of flexible tubing. In other embodiments, the cover is further comprised of a port and flow shutoff means, wherein the flow shutoff means halts or inhibits the application of reduced pressure to the cover when exudate from the wound reaches a predetermined level within the cover. In yet other embodiments of this second version of the invention, the reduced pressure under the cover at the site of the wound is in the range from approximately 20 mm of Hg below atmospheric pressure to approximately 125 mm of Hg below atmospheric pressure. In other embodiments, the reduced pressure is applied in a cyclic nature, the cyclic nature providing alternating time periods of application of reduced pressure and without application of reduced pressure.

In a third version of the present invention, an appliance for administering reduced pressure treatment to a wound on a body is comprised of a treatment device and a vacuum system. In various embodiments of this third version of the invention, the treatment device is also comprised of a cover and sealing means, which may have substantially the same structure, features, characteristics and operation as the cover and sealing means, respectively, described above in connection with the first and second versions of the present invention. In the various embodiments of this third version of the invention, the vacuum system is comprised of a suction bulb, which may (but not necessarily) provide a source of reduced pressure, and reduced pressure supply means, which are described in more detail below, to operably connect the cover to the suction bulb, so that the site of the wound in the volume under the cover may be supplied with reduced pressure by the suction bulb. In some embodiments of this third version of the invention, the suction bulb is further comprised of an inlet port and an outlet port, wherein the inlet port is operably connected to the reduced pressure supply means, and the vacuum system further comprises an exhaust tubing member operably connected to the outlet port. In some of these embodiments, the vacuum system further comprises an exhaust control valve operably connected to the exhaust tubing member. In other embodiments, the vacuum system is further comprised of a filter operably connected to the exhaust tubing member, which prevents the venting of micro-organisms or fluids (or both) aspirated from the wound. In yet other embodiments, the vacuum system is further comprised of a supplemental vacuum system that is operably connected to the exhaust tubing member. In these embodiments, the supplemental vacuum system may generally have substantially the same structure, features, characteristics and operation as the vacuum system described above in connection with the second version of the invention.

A fourth version of the present invention discloses a method of treating a wound. In one embodiment of this fourth version of the invention, the method comprises the following steps. First, a cover is positioned on the body over the wound, wherein the cover may have substantially the same structure, features, characteristics and operation as the embodiments of the cover described above in connection with the first, second and third versions of the invention. Second, the cover is operably sealed to the body so that reduced pressure may be maintained in the volume under the cover at the site of the wound. Third, the cover is operably connected with a vacuum system for producing reduced pressure in the volume under the cover at the site of the wound. Fourth, the reduced pressure is maintained until the wound has progressed toward a selected stage of healing. In other embodiments of this fourth version of the invention, the vacuum system is comprised of a suction bulb and the method further comprises the step of squeezing the suction bulb to reduce its volume and then releasing the suction bulb, so that reduced pressure is produced in the volume under the cover at the site of the wound. In other embodiments of this fourth version of the invention, the reduced pressure under the cover at the site of the wound is in the range from approximately 20 mm of Hg below atmospheric pressure to approximately 125 mm of Hg below atmospheric pressure. In still other embodiments of this fifth version of the invention, the reduced pressure is applied in a cyclic nature, the cyclic nature providing alternating time periods of application of reduced pressure and without application of reduced pressure. In other embodiments, the cover is further comprised of a lid member, a cup body member, and lid attachment means to removably attach the lid member to the cup body member, and the method further comprises the steps of halting the application of reduced pressure to the cover, removing the lid member from the cup body member, and attending to the wound. In some of these embodiments, the method further comprises the steps of re-attaching the lid member to the cup body member after attending to the wound and then reapplying reduced pressure to the volume under the cover in the area of the wound. In still other embodiments of this fourth version of the invention, the top cup member further comprises a port and flow shutoff means operably connected to the port, wherein the flow shutoff means halts or hinders the supply of reduced pressure to the volume under the cover in the area of the wound when the level of exudate within the cover reaches a predetermined level. In these embodiments, the method may further comprise the steps of monitoring the level of exudate aspirated from the wound that accumulates within the volume of the cover and removing the cover from the body when the level of exudate aspirated from the wound causes the flow shutoff means to halt or hinder the supply of reduced pressure to the volume under the cover in the area of the wound. It is to be noted that in various other embodiments the steps described above may be performed in a different order than that presented.

The present invention therefore meets the needs discussed above in the Background section. For example, some embodiments of the present invention can eliminate the requirement for a separate collection device to collect exudate from the wound because the exudate is collected and retained within the volume under the cover. In these embodiments, the interface member is sealed to the body by the sealing means and exudate from the wound flows from the wound through the flow control means in the interface member into the volume of the cover above the interface member. The flow control means do not allow the exudate to flow back into the area of the wound under the interface member. Thus, this type of device could reduce the expense involved in wound treatment by eliminating the need for the collection device. This treatment device also removes exudate from the presence of the wound to aid in wound healing. It is also possible for this type of treatment device to be disposable. Further, some embodiments of the treatment device allow for physical access to the wound without the need for removing the treatment device from the body. In these embodiments, the lid member may be removed from the cup body member of the cover, exposing the area of the wound if an interface member is not utilized. This embodiment of the device could enhance patient comfort because it would not be necessary to remove the sealing means to access the wound. In addition, because access is simple and quickly obtained, the present invention may also decrease the cost of wound treatment by reducing the time required of healthcare practitioners to be involved in wound treatment. The present invention should also be relatively inexpensive to produce, while meeting the needs described above. Finally, as can be observed from the foregoing discussion, the present invention has great flexibility. In various embodiments, it may be used with or without the interface member, as well as with or without the removable lid feature.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which.

DETAILED DESCRIPTION OF THE PREFERRED EMBODIMENT

Figure 1:
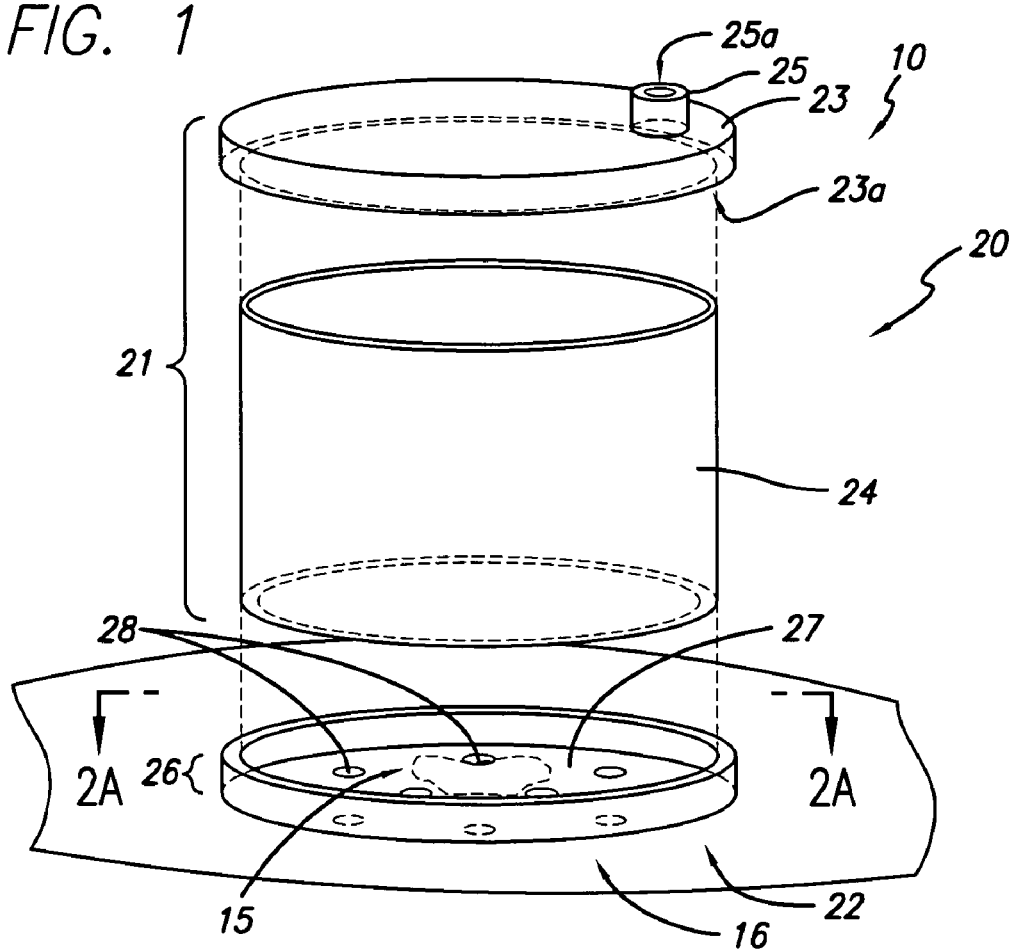
FIG. 1 is an exploded perspective view of an embodiment of a cover comprising the present invention, as such cover would appear from above the body of a patient while the cover is positioned on the body.

In accordance with the present invention, a wound treatment appliance is provided for treating a wound by applying reduced pressure (i.e., pressure that is below ambient atmospheric pressure) to the wound in a controlled manner for a selected time period in a manner that overcomes the disadvantages of currently existing apparatus. One embodiment of a first version of the invention is the treatment appliance 10 illustrated in FIG. 1. FIG. 1 is an exploded perspective view of a cover 20 comprising the treatment appliance 10 from the side of and above the cover 20 as it appears when applied to a portion of the body 16 of a patient surrounding a wound 15. In this embodiment, the cover 20 is comprised of a top cup member 21, an interface member 22, and interface attachment means, which are described in more detail below, to attach the interface member 22 to the top cup member 21. This embodiment also comprises sealing means to seal the cover 20 to the portion of the body 16 surrounding the wound 15, which are described in more detail below, and reduced pressure supply means (not illustrated), which are also described in more detail below. The cover 20 is generally sized to be placed over and enclose the wound 15 to be treated. The cover 20 and the sealing means (described in more detail below) allow reduced pressure to be maintained in the volume under the cover 20 at the site of the wound 15 to be treated, as described in more detail below. The reduced pressure supply means are used to operably connect the cover 20 to a reduced pressure supply source (also not illustrated) in a manner so that the reduced pressure supply source provides a supply of reduced pressure to the cover 20, so that the volume under the cover 20 at the site of the wound 15 may be maintained at reduced pressure. It is to be noted, however, that in other embodiments of the present invention, the top cup member 21 may be used for treatment of a wound 15 without the interface member 22. In these embodiments, the top cup member 21 alone is placed over the wound 15 and reduced pressure is applied to the volume under the top cup member 21.

Figure 5:
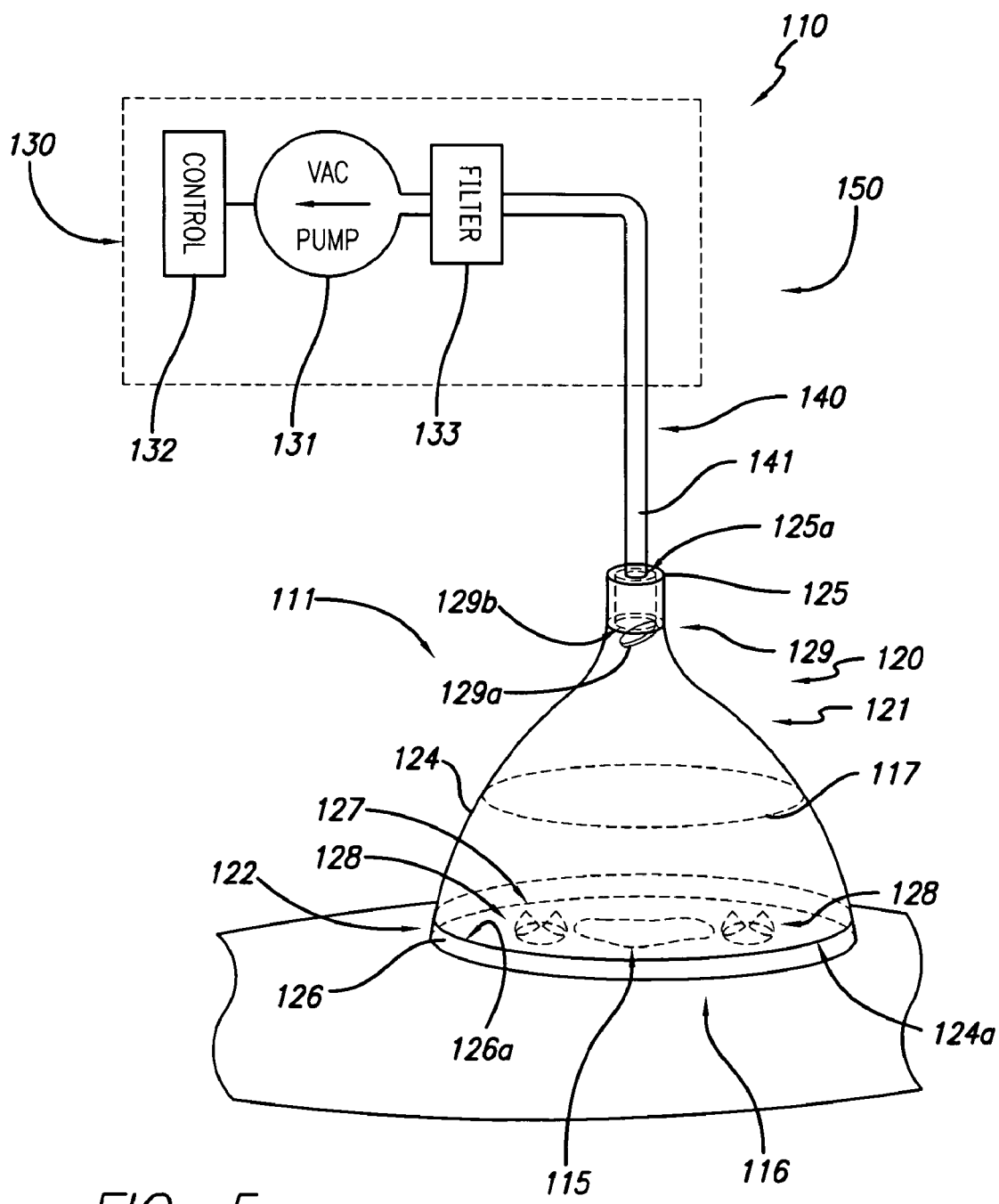
FIG. 5 is a view of an embodiment of a treatment appliance comprising the present invention, in which an embodiment of a treatment device, shown in perspective view, is placed over a wound on a body, and in which an embodiment of a vacuum system, depicted generally and shown in schematic elevation view, provides reduced pressure within the volume under a cover comprising the treatment device.

The embodiment of the top cup member 21 of the cover 20 illustrated in FIG. 1 is further comprised of a lid member 23 and a cup body member 24. In this embodiment, the lid member 23 is removably or permanently attached to the cup body member 24 using lid attachment means, which may be substantially the same as any of the interface attachment means, which are described in more detail below. While the lid member 23 is attached to the cup body member 24, the lid attachment means provides a gas-tight and liquid-tight seal so that reduced pressure may be maintained in-the volume under the cover 20 in the area of the wound 15. In the embodiment illustrated in FIG. 1, the top cup member 21 is approximately cylindrical in shape. In other embodiments of this first version of the present invention, the top cup member 21 may be of almost any shape or combination of shapes, as long as the open end 23a of the lid member 23 is of a size and shape adapted to fit against a portion of the surface of the cup body member 24 in a manner so that an airtight and liquid-tight seal can be maintained by the use of the lid attachment means, as described in more detail below. For example, as illustrated in FIG. 5, the top cup member 121 of the cover 120 may be approximately cup-shaped, having an interface member 122 disposed on its bottom surface. As other examples, the cover 20, 120 may be cubical, spherical, spheroidal, hexahedral, polyhedral, or arcuate in shape, or may be comprised of any combination of such shapes, in other embodiments. Thus, referring again to FIG. 1 as an example, the lid member 23 may also be shaped approximately as a hemisphere or a cone in other embodiments. As another example, in yet other embodiments, the cup body member 24 and the open end 23a of the lid member 23 may have a cross-section of approximately elliptical, square, rectangular, polygonal, arcuate or other shape or combination of all such shapes. The preferred shape and size of the top cup member 21, 121, as well as the size and shape of any lid member 23 comprising it, are dependent upon the materials comprising the cover 20, 120, the thickness of the cover 20, 120, the nature of the wound to be treated, the size, shape and contour of the portion of the body to be covered by the cover 20, 120, the magnitude of the reduced pressure to be maintained under the cover 20, 120, the size, shape and other aspects of the interface portion 22, 122, the individual preferences of the user of the cover 20, 120, and other factors related to access to the wound 15, the sealing means, and the reduced pressure supply means, as described in more detail below.

Figure 2A:
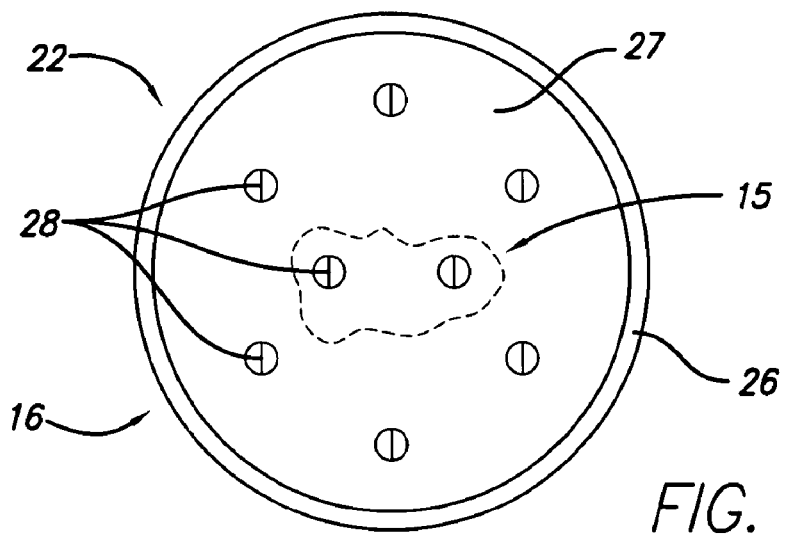
FIG. 2A is an plan view of the interface member of the embodiment of the cover illustrated in FIG. 1, as taken along the lines 2A-2A of FIG. 1.
Figure 2B:
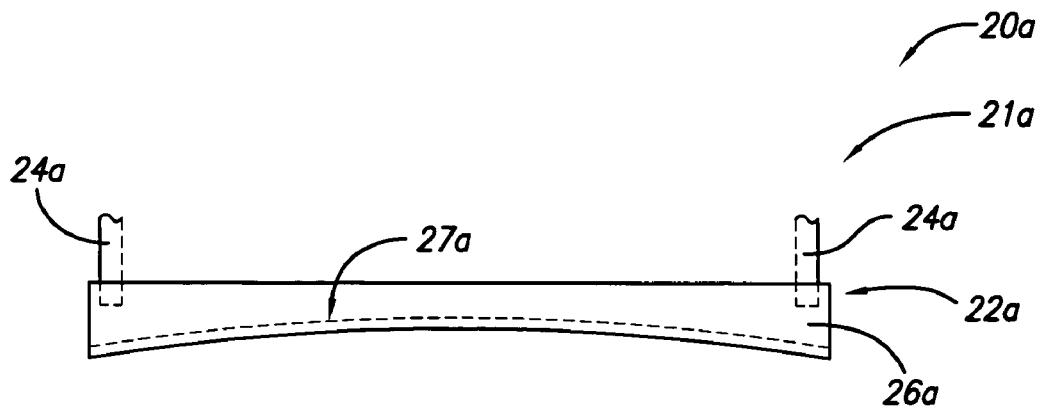
FIG. 2B is an elevation view of another embodiment of an interface member.

In the embodiment of the cover 20 illustrated in FIG. 1, the lid member 23 may be detached from the cup body member 24. This allows the user of the appliance 10 to have access to the area of the wound 15 without having to break the sealing means used to operably seal the cover 20 to the portion of the body 16 surrounding the wound 15. The ability to access the wound 15 in this manner results in more efficient use of the time of healthcare practitioners and less discomfort to patients. It is to be noted that in other embodiments, the lid member 23 and the cup body member 24 may be permanently attached together or may be formed as a single piece. For example, the top cup member 121 of the cover 120 of FIG. 5 does not have a detachable lid member, but is instead formed as a single piece. In these embodiments, and referring to the cover 20 of FIG. 1 as an example, the lid member 23 and the cup body member 24 may be fabricated as a single piece, such as by injection molding, or they may be attached together by any appropriate means, such as by welding, fusing, adhesives, glues, bolts, screws, pins, rivets, clamps, or other fasteners or means or combinations of all such means. In the embodiment of the present invention illustrated in FIG. 1, the lid member 23 and the cup body member 24 are each constructed of a material that is rigid enough to support the cover 20 away from the wound 15. Thus, the lid member 23 and the cup body member 24 of the cover 20 may be comprised of almost any rigid or semi-rigid medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the cover 20 away from the wound 15. For example, the lid member 23 and the cup body member 24 may each be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. It is to be noted that in various embodiments of this first version of the invention, the lid member 23 and the cup body member 24 may be constructed in whole or in part of gas-permeable materials, allowing limited amounts of oxygen to penetrate the lid member 23 and the cup body member 24 so that the portion of the body under the cover 20 in the area of the wound 15 can "breathe." In some embodiments, all portions of the top cup member 21 are preferably constructed of one type of semi-rigid material, such as polypropylene. In other embodiments, the top cup member 21 may be constructed of more than one material. For example, the lid member 23 may be constructed of silicone and the cup body member 24 of the cover 20 may be comprised of polyvinyl chloride, so that the lid member 23 may be stretched enough to overlap and seal against the outer edge of the cup body member 24 to form an operable seal, as described in more detail below. The preferred wall thickness of the cover 20 and its various component parts is dependent upon the size and shape of the cover 20, the size, shape and contour of the portion of the body to be covered by the cover 20, the magnitude of the reduced pressure to be maintained under the cover 20, the materials comprising the cover 20, and the individual preferences of the user of the cover 20. For example, in the embodiment of the cover 20 illustrated in FIG. 1, for a top cup member 21 constructed entirely of a silicone blend and having an approximate diameter of 4 inches and an approximate height of 3 inches, the preferred wall thickness of the top cup member 21 is in the range from $1/32$ inches to $3/8$ inches. It is to be noted that in other embodiments the wall thickness of the various portions of the top cup member 21 may vary from embodiment to embodiment, as well as from portion to portion of the top cup member 21. Generally, the top cup member 21 of the illustrated embodiment may be constructed using any suitable means currently known in the art or that may be developed in the art in the future. For example, a top cup member 21 constructed entirely of a silicone blend may be manufactured by means of injection molding. As another example, embodiments of covers 20 constructed of different types of materials may be constructed in the manner described above in this paragraph. It is to be noted that embodiments of the top cup member 121 comprised of one piece, without separate lid member and cup body member as illustrated by the cover 120 of FIG. 2, the top cup member may be constructed of substantially the same materials, have the same wall thicknesses, and be constructed in substantially the same manner as described above in this paragraph.

In some embodiments of this first version of the present invention, as illustrated in FIG. 1, the cover 20 further comprises a port 25. The port 25 is adapted to be of a size and shape so that the reduced pressure supply means may be operably connected to the top cup member 21 by means of the port 25. When the port 25 is operably connected to the reduced pressure supply means, reduced pressure may be supplied to the volume under the cover 20 at the site of the wound 15 to be treated. Although the port 25 is positioned at a location near one side of the lid member 23 of the enclosure 20 in the embodiment illustrated in FIG. 1, the port 25 may be located at other positions on the top cup member 21 (on either the lid member 23 or the cup body member 24) in other embodiments, as long as the port 25 does not adversely affect the ability of the cup body member 24 to form an operable seal with the lid member 23 or the interface member 22, as described in more detail below. Although the port 25 may be constructed of a material different from the material comprising the remainder of the top cup member 21 in various embodiments of the invention, the port 25 is preferably constructed from the same material comprising the top cup member 21 of the cover 20. In the embodiment of the cover 20 illustrated in FIG. 1, the port 25 is generally cylindrical in shape and is further comprised of an approximately cylindrical channel 25a that extends from the top of the port 25 to the bottom of the port 25. The port 25 of this embodiment is thus able to receive a vacuum system or reduced pressure supply means, which are described in more detail below, adapted to be connected to this shape of port 25 and channel 25a. In other embodiments of this first version of the invention, the port 25 or the channel 25a or both may have different shapes and configurations as may be desired to adapt and connect the port 25 and the channel 25a to the vacuum system or reduced pressure supply means, which are described in more detail below. In some of the embodiments comprising a port 125, as illustrated in the embodiment of the cover 120 of FIG. 5, the top cup member 121 may be further comprised of flow shutoff means (a one-way valve 129 in this embodiment), which are operably connected to the port 125 and described in more detail below. Referring again to FIG. 1 as an example, in other embodiments of this first version of the invention, a means of connecting the top cup member 21 to the reduced pressure supply means (described in more detail below) may be located on the top cup member 21 in lieu of or in conjunction with the port 25. For example, in some embodiments, the port 25 may be combined with a variable descending diameter adapter (commonly referred to as a "Christmas tree" adapter), a luer lock fitting, or other similar adapter or fitting.

In the embodiment of the cover 20 illustrated in FIG. 1, the interface member 22 is removably attached to the cup body member 24 by the interface attachment means (described in more detail below), which are used to make an approximately airtight and liquid-tight seal with the top cup member 21. In the illustrated embodiment, the interface member 22 is comprised of a border portion 26, a membrane portion 27, and membrane flow control means, which are described in more detail below. The membrane portion 27 in the illustrated embodiment has an approximately flat surface and is approximately circular in shape when viewed from above. In other embodiments, the membrane portion 27 may have other shapes. For example, the surface of the membrane portion 27 may have a curved surface, so that it is concave (similar to a concave lens) in shape. In addition, the interface member 22 (and its border portion 26 and membrane portion 27) may be of almost any shape and size, as long as the interface member 22 is of a size and shape adapted so that it fits against a portion of the surface of the top cup member 21 in a manner so that an approximately airtight and liquid-tight seal is maintained by the interface attachment means, as described in more detail below. For example, when viewed from above, the interface member 22 may have an approximately elliptical, square, rectangular, polygonal, arcuate or other shape or combination of all such shapes. As another example, as illustrated in the embodiment of the interface member 22a of the cover 20a illustrated in FIG. 2B, when viewed from the side, the interface member 22a may appear to have an approximately curved surface so that it may rest on portions of the body that have an approximately curved surface. Thus, in the illustrated embodiment, the border portion 26a has a generally flat top surface and an approximately concave lower surface bounding the membrane portion 27a. Also in this embodiment, the interface member 22a is removably attached to the cup body portion 24a of the top cup member 21a using the interface attachment means, which are described in more detail below. It is to be noted that in some embodiments, as illustrated by the embodiment of the cover 120 in FIG. 5, the top surface of the border portion 126 of the interface member 122 may be positioned adjacent to the bottom surface of the top cup member 121. The preferred shape and size of the interface member 22, 22a, 122, as well as the size and shape of the border portion 26, 26a, 126 and membrane portion 27, 27a, 127 comprising it, are dependent upon the size and shape of the top cup member 21, 21a, 121, materials comprising the cover 20, 120, the thickness of the interface member 22, 22a, 122, the nature of the wound to be treated, the size, shape and contour of the portion of the body to be covered by the cover 20, 20a, 120, the magnitude of the reduced pressure to be maintained under the cover 20, 20a, 120, the individual preferences of the user of the cover 20, 20a, 120, and other factors related to the sealing means and interface attachment means, as described in more detail below.

In the embodiment of the present invention illustrated in FIG. 1, the border portion 26 is constructed of a material that is rigid enough to support the interface member 22 and the cover 20 away from the wound. Thus, the border portion 26 of the cover 20 may be comprised of almost any rigid or semi-rigid medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the cover 20 away from the wound. For example, the border portion 26 may be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. In the illustrated embodiment, the membrane portion 27 is constructed of a material that is strong enough to support the membrane flow control means, which are described in more detail below. Thus, the membrane portion 27 of the cover 20 may be comprised of almost any rigid, semi-rigid, or flexible medical grade material that is currently known in the art or that may be developed in the art in the future, as long as such material is liquid-impermeable, suitable for purposes of wound treatment (e.g., can be sterilized and does not absorb significant amounts of fluids, such as wound exudate), and is capable of supporting the membrane flow control means, which are described in more detail below. For example, the membrane portion 27 may be comprised of rubber (including neoprene), metal, wood, paper, ceramic, glass, or rigid or semi-rigid polymer materials, such as polypropylene, polyvinyl chloride, silicone, silicone blends, or other polymers or combinations of all such polymers. It is to be noted that in various embodiments of this first version of the invention, the interface member 22 may be constructed in whole or in part of gas-permeable materials, allowing limited amounts of oxygen to penetrate the interface member 22 so that the portion of the body under the cover 20 can "breathe." In some embodiments, all portions of the interface member 22 are preferably constructed of one type of semi-rigid material, such as polypropylene. In other embodiments, the interface member 22 may be constructed of more than one material. For example, the membrane portion 27 may be constructed of silicone and the border portion 26 of the cover 20 may be comprised of polyvinyl chloride, so that the membrane portion 27 may be more flexible than the border portion 26. The preferred wall thickness of the interface member 22 and its various component parts is generally dependent upon the same parameters as described above for the top cup member 21. Although the interface member 22 need not be constructed of the same materials as the top cup member 21, it is preferred that the interface member 22 be constructed of the same materials as the top cup member 21. Generally, the interface member 22 of the illustrated embodiment may be constructed using any suitable means currently known in the art or that may be developed in the art in the future. For example, an interface member 22 constructed entirely of one material may be manufactured by means of injection molding. As another example, the component parts of an interface member 22 constructed of different types of materials may be attached together by any appropriate means, such as by welding, fusing, adhesives, glues, bolts, screws, pins, rivets, clamps, or other fasteners or other means or combinations of all such means.

Referring to the embodiment of the cover 20 illustrated in FIG. 1, the interface member 22 is further comprised of membrane flow control means, which allow exudate aspirated from the wound 15 to flow into the volume of the top cup member 21, but not in the opposite direction. In the illustrated embodiment, the membrane flow control means is comprised of eight flow control valves 28. It is to be noted that in various embodiments the flow control valves 28 may be any type of valve currently known in the relevant art or that may be developed in the relevant art in the future that is suitable for operation in reduced pressure environments that allows fluids to flow in one direction through the valve, but not in the opposite direction. For example, such valves 28 may generally be comprised of sprung or unsprung flapper or disc-type valves. In the illustrated environment, the flow control valves 28 are comprised of flapper-type valves, which are each further comprised of two flappers that are approximately semi-circular in shape and hinged at their outside edge so that when they fall together they form a seal that only allows fluids to flow in one direction (from the wound 15 to the volume within the top cup member 21 in this embodiment). Although the interface member 22 may have at least one flow control valve 28 in some embodiments, the interface member 22 may have almost any number of flow control valves 28 in other embodiments. For example, as illustrated in FIG. 5, the interface member 122 may be comprised of two flow control valves 128. In embodiments of the present invention comprising flow control valves 28, the preferred number and type of valves 28 is dependent upon the shape and size of the interface member 22, the materials comprising the interface member 22, the thickness of the membrane portion 27, the nature of the wound 15 to be treated, the amount of exudate anticipated, the size, shape and contour of the portion of the body to be covered by the cover 20, the magnitude of the reduced pressure to be maintained under the cover 20, the individual preferences of the user of the cover 20, and other factors related to the sealing means, as described in more detail below. It is to be noted that in some embodiments, the flow control valves 28 may be formed from a single piece with the membrane portion 27, or may be attached to the membrane portion 27 using any suitable means, such as by welding, fusing, adhesives, glues, bolts, screws, pins, rivets, clamps, or other fasteners or means or combinations of all such means. In other embodiments, the membrane flow control means may be comprised of a membrane portion 27 that is constructed in whole or in part of a material that allows fluids to flow in one direction, but not in the opposite direction. In these embodiments, exudate from the wound 15 flows from the wound 15 through the membrane portion 27 (or a portion thereof) to the volume within the top cup member 21, but does not flow in the reverse direction back to the wound 15.

Figure 3:
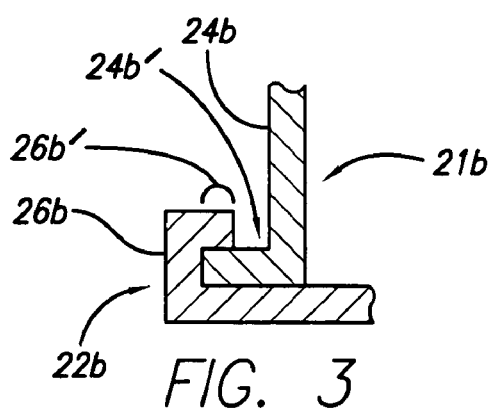
FIG. 3 is an enlarged cross-sectional elevation view of one embodiment of the interface attachment means comprising the present invention.
Figure 4:
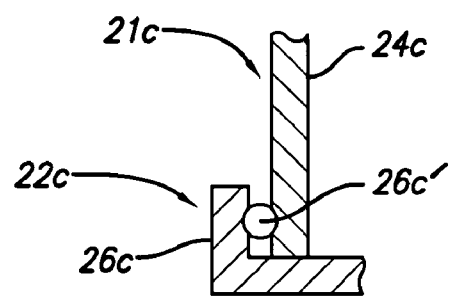
FIG. 4 is an enlarged cross-sectional elevation view of another embodiment of the interface attachment means comprising the present invention.

In various embodiments of this first version of the present invention, the interface attachment means, which may be used to removably or permanently attach the interface member 22 to the top cup member 21, may be any suitable means currently known in the relevant art or developed in the relevant art in the future that may be used to create an airtight and liquid-tight seal (sometimes referred to herein as an "operable seal") between the interface member 22 and the top cup member 21. For example, in the embodiment illustrated in FIG. 3, which is an enlarged cross-sectional elevation view of an interface attachment means, the border portion 26b is constructed of a semi-rigid material (such as silicone) and has a lip portion 26b' that extends around the perimeter of the interface member 22b. The cup body member 24b of the top cup member 21b also has a lip portion 24b' adjacent to the bottom edge of the cup body member 24b that extends around the perimeter of the bottom edge of the cup body member 24b. In this embodiment, the interface attachment means is comprised of the lip portion 26b' of the interface member 22b being stretched over the lip portion 24b' of the top cup member 21, so that the lip portions are joined tightly together to form an operable seal. As another example, as illustrated in FIG. 4, the interface attachment means may be comprised of an o-ring (or gasket or similar sealing means) 26c' that is positioned in a groove extending around the perimeter of the border portion 26c or the cup body member 24c or both, so that the o-ring 26c' forms an operable seal between the top cup member 21c and the interface member 22c. Referring again to FIG. 1 as an example, in still other embodiments, the exterior bottom portion of the cup body member 24 may be threaded and the interior bottom portion of the border portion 26 of the interface member 22 may be of a structure to receive such threads, so that an operable seal is created when the cup body member 24 is screwed into the interface member 22. In yet other embodiments, as illustrated in FIG. 5, the interface attachment means may be comprised of a magnetic strip (not shown) attached to the bottom surface 124a of the cup body member 124 of the top cup member 121 and to the top surface 126a of the border portion 126 of the interface member 122, so that such surfaces abut against one another in the manner illustrated in FIG. 5 when the surfaces are attracted by magnetic force, creating an operable seal. Further, the interface attachment means may be comprised of a washer, gasket, o-ring or similar structure (not shown) attached to the bottom surface 124a of the cup body member 124 of the top cup member 121 or to the top surface 126a of the border portion 126 of the interface member 121, or both, so that such surfaces abut against one another in the manner illustrated in FIG. 5, creating an operable seal. In these embodiments, the top cup member 121 may be held in place against the interface member 122 by means of clips, brackets, pins, clamps, clasps, adhesives, adhesive tapes, quick-release or other fasteners, or combinations of such means. In addition, many types of sealing means that may be used to removably attach components of kitchenware-type items together may by used as the interface attachment means. It is also to be noted that in other embodiments the interface attachment means may be comprised of means to permanently attach the interface member 22 to the top cup member 21 or of forming the interface member 22 and the top cup member 21 as a single piece. In these embodiments, and referring to the cover 20 of FIG. 1 as an example, the interface member 22 and the top cup member 21 may be fabricated as a single piece, such as by injection molding, or they may be attached together by any appropriate means, such as by welding, fusing, adhesives, glues, bolts, screws, pins, rivets, clamps, or other fasteners or means or any combinations of all such means. Referring again to FIG. 1 as an example, it is to be noted that the lid attachment means that may be used to removably or permanently attach the lid member 23 to the cup body member 21 may have substantially the same structure, features, characteristics and operation as any or all of the embodiments comprising the interface attachment means described above.

An embodiment of a second version of the present invention is the treatment appliance 110 illustrated in FIG. 5. In this embodiment, the treatment appliance 110 is comprised of a treatment device 111 and a vacuum system, generally designated 150, which is operably connected to, and provides a supply of reduced pressure to, the treatment device 111. Also in this embodiment, the treatment device 111 is comprised of a cover 120. In addition, in this embodiment, the vacuum system 150 is further comprised of a reduced pressure supply source, generally designated 130, which is illustrated schematically and described in more detail below, and reduced pressure supply means, generally designated 140, which are described in more detail below. Also in this embodiment, the reduced pressure supply means 140 are used to connect the reduced pressure supply source 130 to the cover 120 in a manner so that reduced pressure is supplied to the volume under the cover 120 at the site of the wound 115 to be treated, as described in more detail below. In the embodiment of the second version of the invention illustrated in FIG. 5, the illustrated cover 120 is comprised of a top cup member 121, an interface member 122, and interface attachment means to removably attach the top cup member 121 to the interface member 122. In the illustrated embodiment, the interface attachment means is comprised of a magnetic strip (not shown) on the top surface 126a of the border portion 126 of the interface member 122 and a magnetic strip (not shown) on the bottom surface 124a of the cup body member 124 of the top cup member 121. An operable seal is formed between the interface member 122 and the top cup member 121 by the magnetic attraction of the magnetic strips. In other embodiments, the interface attachment means may be comprised of any of the interface attachment means of the first version of the present invention illustrated and described above in connection with FIG. 1 through FIG. 5. Alternatively, the interface member 122 and the top cup member 121 may be formed as a single piece or permanently attached, as illustrated and described above in connection with FIG. 1 through FIG. 5. It is to be noted that in this and other embodiments of this second version of the invention, the cover 120 may have substantially the same structure, features, characteristics and operation as any embodiment of any of the covers 20, 20a, 120 of the first version of the invention described above and illustrated in connection with FIG. 1 through FIG. 5. It is also to be noted that in other embodiments of the present invention, the top cup member 121 may be used for treatment of a wound 115 without the interface member 126. In these embodiments, the top cup member 121 alone is placed over the wound 115 and reduced pressure is applied to the volume under the top cup member 121.

In the various embodiments of this second version of the present invention, as illustrated in FIG. 5, the interface member 122 of the cover 120 may be comprised of a semi-rigid material and the sealing means may be comprised of the suction of the interface member 122 against the portion 116 of the body adjacent to the interface member 122 of the cover 120, such suction being produced by the presence of reduced pressure in the volume under the cover 120 at the site of the wound 115. In other embodiments, the sealing means may be comprised of an adhesive, an adhesive tape, lanoline, or other sealant, or any combination of such means, that is disposed between the interface member 122 and the portion 116 of the body adjacent to the interface member 122 or disposed over the interface member 122 and the portion of the body outside the perimeter of the interface member 122. In yet other embodiments, the sealing means may be comprised of a material (not illustrated) that is positioned approximately over the cover 120 and wrapped around the portion 116 of the body on which the cover 120 is positioned. This material is used to hold the cover 120 against the adjacent portion 116 of the body. For example, if the wound 115 were on the patient's leg, an elastic bandage or adhesive tape may be wrapped over the cover 120 and around the leg.

In the embodiment illustrated in FIG. 5, the reduced pressure supply source 130 of the vacuum system 150, which produces a source of reduced pressure or suction that is supplied to the cover 120, is comprised of a vacuum pump 131, a control device 132, and a filter 133. Although the preferred means of producing the reduced pressure or suction is a vacuum pump 131 in this embodiment, in other embodiments of this second version of the invention other means may be used, such as an outlet port of a centralized hospital vacuum system. In the illustrated embodiment, predetermined amounts of suction or reduced pressure are produced by the vacuum pump 131. The vacuum pump 131 is preferably controlled by a control device 132, such as a switch or a timer that may be set to provide cyclic on/off operation of the vacuum pump 131 according to user-selected intervals. Alternatively, the vacuum pump 131 may be operated continuously without the use of a cyclical timer. In addition, in some embodiments the control device 132 may provide for separate control of the level of reduced pressure applied to the volume under the cover 120 at the site of the wound 115 and the flow rate of fluid aspirated from the wound 115, if any. In these embodiments, relatively low levels of reduced pressure may be maintained at the site of the wound 115 in the volume under the treatment device 111, while still providing for the removal of a relatively large volume of exudate from the wound 115. A filter 133, such as a micropore filter, is preferably attached to the inlet of the vacuum pump 131 to prevent potentially pathogenic microbes or aerosols from contaminating, and then being vented to atmosphere by, the vacuum pump 131. In other embodiments, the filter 133 may also be a hydrophobic filter that prevents any exudate from the wound 115 from contaminating, and then being vented to atmosphere by, the vacuum pump 131. It is to be noted that in other embodiments of the invention, the reduced pressure supply source 130 may not have a filter 133 or a control 132 or any combination of the same.

In other embodiments of the second version of the invention, the reduced pressure supply source 130 of the vacuum system 150, may be comprised of a small, portable vacuum pump 131. In some of these embodiments, a filter 133 or a power source (not illustrated), or both, may also be contained within the housing for the portable vacuum pump 131. In these embodiments, the portable vacuum pump 131 is preferably controlled by a control device 132 that is also located within the housing for the portable vacuum pump 131, which may provide substantially the same functions as the control device 132 described above. Except for its smaller size, the portable vacuum pump 131 may operate in substantially the same manner as the vacuum pump 131 described above. Also, in these embodiments, the filter 133 may have the same structure, features, characteristics and operation, and provide substantially the same functions, as the filter 133 described above. In some of these embodiments, the filter 133 may be rigidly connected to the portable vacuum pump 131. The power source may be any source of energy currently known in the art or that may be developed in the art in the future that may be used to power the portable vacuum pump 131. For example, in some embodiments, the power source may be a fuel cell, battery or connection to a standard wall electrical outlet.

In the embodiment of the second version of the invention illustrated in FIG. 5, the reduced pressure supply means 140 of the vacuum system 150, which are used to connect the reduced pressure supply source 130 to the cover 120 so that reduced pressure is supplied to the volume under the cover 120 at the site of the wound 115, is comprised of at least one tubing member 141. In this embodiment, the at least one tubing member 141 is sufficiently flexible to permit movement of the at least one tubing member 141, but is sufficiently rigid to resist constriction when reduced pressure is supplied to the cover 120 or when the location of the wound 115 is such that the patient must sit or lie upon the at least one tubing member 141 or upon the treatment device 111. In the embodiment illustrated in FIG. 5, the at least one tubing member 141 is connected to the cover 120 by inserting one end of the at least one tubing member 141 into an opening 125a of a port 125 of the cover 120. In this embodiment, the at least one tubing member 141 is held in place in the opening 125a by means of an adhesive. It is to be noted that in other embodiments of this second version of the invention, the at least one tubing member 141 may be connected to the port 125 of the cover 120 using any suitable means currently known in the art or developed in the art in the future. Examples include variable descending diameter adapters (commonly referred to as "Christmas tree" adapters), luer lock fittings and adapters, clamps, and combinations of such means. Alternatively, the port 125 and the at least one tubing member 141 may be fabricated as a single piece. Similar means may be used to connect the other end of the at least one tubing member 141 to the vacuum pump 131 or other reduced pressure supply source 130 providing the reduced pressure.

In the embodiment of the second version of the present invention illustrated in FIG. 5, the treatment device 111 functions to actively draw fluid or exudate from the wound 115 through two flow control valves 128 positioned on the membrane portion 127 of the interface member 122 into the interior volume of the cover 120. In this embodiment, it is generally desirable to collect exudate in the interior volume of the cover 120, but not to allow the exudate to flow into the reduced pressure supply means 140 in order to prevent clogging of the vacuum pump 131. In addition, it is desirable to halt or inhibit the supply of reduced pressure to the cover 120 in the event that the exudate aspirated from the wound 115 exceeds a predetermined quantity. Further, it is desirable to interrupt the application of suction to the cover 120 to prevent exsanguination in the unlikely event a blood vessel ruptures under the cover 120 during treatment. If, for example, a blood vessel ruptures in the vicinity of the cover 120, a shutoff mechanism would be useful to prevent the vacuum system 150 from aspirating any significant quantity of blood from the patient. As a result, the top cup member 121 in the illustrated embodiment is further comprised of flow shutoff means. In this embodiment, the flow shutoff means is comprised of a flapper-type valve 129, which is generally comprised of a flapper 129a that is hinged to an interior surface of the port 125 and seats against a stop 129b. The flapper 129a is buoyant when compared to the exudate, so that it floats upon the exudate as the level of exudate in the volume of the cover 120 rises to the level of the flapper valve 129. The flapper 129a is, however, heavy enough not to be drawn against the stop 129b when reduced pressure is applied to the cover 120 by the vacuum system 150. Thus, as the exudate level rises to the level of the stop 129b, the flapper 129a floats upon the exudate until the flapper 129a seats against the stop 129b, which seals the cover 120 so that reduced pressure is no longer supplied to the cover 120 by the vacuum system 150. In other embodiments, the flow shutoff means may be comprised of almost any other type of shutoff valve currently known in the relevant art or that may be developed in the relevant art in the future that is suitable for this purpose and use in a reduced pressure environment. Another example of such valve is a float valve, wherein a float ball floats upon the exudate so that the float ball seals against a seat when the level of exudate reaches a predetermined level. All such valves are well known in the relevant art. In other embodiments, other types of mechanisms may also be employed to detect the liquid level within the cover 120 in order to arrest operation of the vacuum system 150. In addition, in various embodiments of this second version of the invention, the flow shutoff means may be comprised of any means that enables the vacuum system 150 to halt the supply of reduced pressure to the cover 120 at any time that the volume of exudate from the wound 115 exceeds a predetermined amount. Such means may include mechanical switches, electrical switches operably connected to the vacuum system controller 132, optical, thermal or weight sensors operably connected to the vacuum system controller 132, and any other means that are currently known in the relevant art or that may be developed in the relevant art in the future.

In some embodiments of this second version of the invention, the treatment device 111 further comprises tissue protection means (not illustrated) to protect and strengthen the surface tissue of the portions 116 of the body that are adjacent to the cover 120. The tissue protection means protects such tissue by preventing abrasion and maceration of the tissue. Preferably, the tissue protection means is a hydrocolloid material, such as COLOPAST Hydrocolloid 2655, anhydrous lanoline, or any combination of such hydrocolloid materials. More preferably, the tissue protection means is COLOPAST Hydrocolloid 2655. The tissue protection means may be applied to the body tissue to be protected, or it may be applied to the surface of the cover 120 that is to be in contact with the body tissue 116, or both, prior to placing the cover 120 over the wound 115. It is to be noted that application of the tissue protection means to the body tissue 116 that is adjacent to the cover 120 at the site of the wound 115 may only entail application of the tissue protection means to the parts of the body tissue 116 adjacent to the cover 120 that require such protection.

Referring to FIG. 5, a method of using the treatment appliance 110 of the illustrated embodiment is also disclosed. In this example, the cover 120 is removed from an aseptic package in which it is stored. The various component parts of the cover are operably sealed together. For example, in the illustrated embodiment, the top cup member 121 is operably sealed to the interface member 122. In embodiments where the top cup member 21 further comprises a lid member 23 and a cup body member 24, as illustrated in FIG. 1, the lid member 23 and the cup body member 24 are also operably sealed together. Referring again to FIG. 5, this sealing of the component parts of the cover 120 may occur before, during or after the cover 120 is placed over the wound 115. The cover 120 is placed over and encloses the wound 115. The cover 120 is connected to the vacuum system 150 by means of the port 125 on the cover 120 either before, after or during the placement of the cover 120 over the wound 115. Where it is deemed necessary by the user of the treatment appliance 110, tissue protection means, as described above, may be placed on a portion of the cover 120, on the body tissue to be protected, or both, prior to placing the cover 120 over the wound 115. Reduced pressure is then supplied to the cover 120 by the vacuum system 150. In the illustrated embodiment, when reduced pressure is applied to the volume under the cover 120 at the site of the wound 115, the cover 120 is drawn downward by the reduced pressure so that the cover 120 is drawn tightly against the surface of the adjacent portion 116 of the body, thus forming an operable seal between the cover 120 and the portion 116 of the body adjacent to the cover 120. References to an "operable seal" and "sealing means" herein refer generally to a seal that may be made gas-tight and liquid-tight for purposes of the reduced pressure treatment of the wound 115. It is to be noted that this seal need not be entirely gas-tight and liquid-tight. For example, the operable seal may allow for a relatively small degree of leakage, so that outside air may enter the volume under the cover 120 at the site of the wound 115, as long as the degree of leakage is small enough so that the vacuum system 150 can maintain the desired degree of reduced pressure in the volume under the cover 120 at the site of the wound 115. As another example, the operable seal formed by the cover 120 may not be solely capable of maintaining the reduced pressure in the volume under the cover 120 at the site of the wound 115 due to the shape of the body portion 116 at the site of the wound 115, due to the orientation of the wound 115, or due to some other reason. In these cases, as well as other cases, it may be necessary or desirable to provide other sealing means (not illustrated), which are described in more detail above. In some embodiments of the second version of the present invention comprising a lid member 23, as illustrated by the cover 20 of FIG. 1, the method may also comprise one or more of the steps of halting the application of reduced pressure to the cover 20, removing the lid member 23 from the cup body member 24, attending to the wound 115, re-attaching the lid member 23 to the cup body member 24, and then reapplying reduced pressure to the volume under the cover 20 in the area of the wound 115. In yet other embodiments, and referring again to FIG. 5, the method may comprise one or more of the steps of monitoring the fluid level 117 in the volume within the cover 120, halting the application of reduced pressure to the cover 120 when the fluid level 117 reaches a predetermined level, removing the fluid in the volume within the cover 120, and reapplying reduced pressure to the volume under the cover 20 in the area of the wound 115. In the preferred embodiments of this second version of the invention, the reduced pressure maintained in the volume under the cover 120 at the site of the wound 115 is in the range from approximately 20 mm of Hg below atmospheric pressure to approximately 125 mm of Hg below atmospheric pressure. In yet other embodiments, the reduced pressure is applied to the cover 120 in a cyclic nature, the cyclic nature providing alternating time periods of application of reduced pressure and non-application of reduced pressure. In various embodiments, the method also comprises the step of maintaining reduced pressure in the volume under the cover 120 at the site of the wound 115 until the wound 115 has progressed toward a selected stage of healing.

Figure 6:
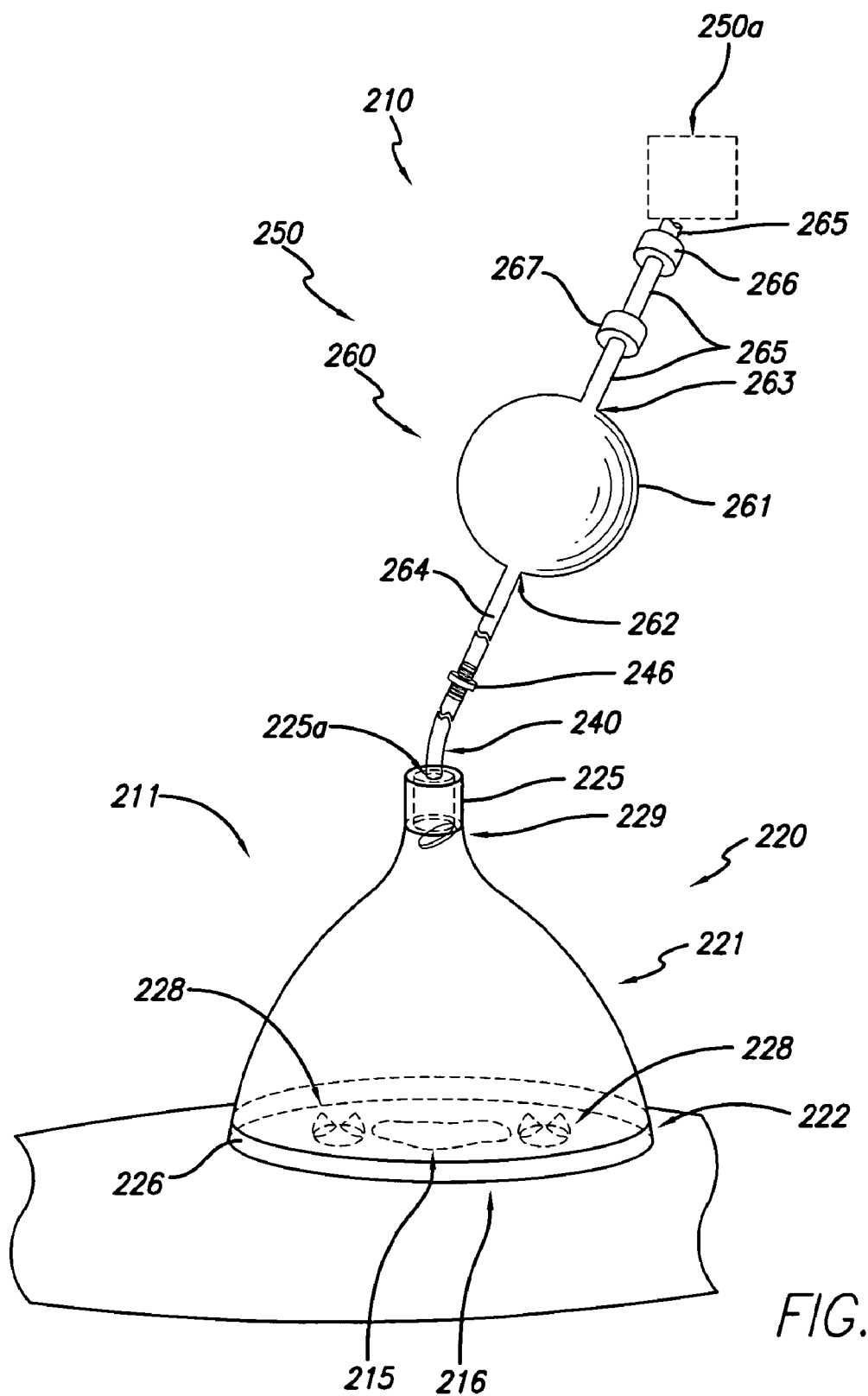
FIG. 6 is a view of an embodiment of a treatment appliance comprising the present invention, in which an embodiment of a treatment device, shown in perspective view from the side of and above the treatment device, is positioned over a wound on a body, and in which an embodiment of a vacuum system, shown in elevational view, provides reduced pressure within the volume under a cover comprising the treatment device.

An embodiment of a third version of the invention is the treatment appliance 210 illustrated in FIG. 6. In this embodiment, the treatment appliance 210 is comprised of a treatment device 211 and a vacuum system, generally designated 250, operably connected to, and providing a supply of reduced pressure to, the treatment device 211. In addition, in this embodiment, the vacuum system 250 is further comprised of a reduced pressure supply source, generally designated 260, which is described in more detail below, and reduced pressure supply means 240, which are described in more detail below. Also in this embodiment, the treatment device 211 is further comprised of a cover 220, which generally has substantially the same structure, features, and characteristics as the embodiment of the cover 120 illustrated and described above in connection with FIG. 5. It is to be noted, however, that in other embodiments of this third version of the invention, the cover 220 may have substantially the same structure, features, characteristics and operation as any embodiment of all of the covers 20, 20a, 120 of the first and second versions of the invention described above and illustrated in connection with FIG. 1 through FIG. 5. In the embodiment illustrated in FIG. 6, the cover 220 is placed over and encloses a wound 215. In the illustrated embodiment, the cover 220 may be sealed to the adjacent portions 216 of the body using any of the sealing means or operable seals described above and illustrated in connection with FIG. 5.

In the embodiment of the third version of the invention illustrated in FIG. 6, the vacuum system 250 is generally comprised of a suction bulb 261 having an inlet port 262 and an outlet port 263, a bulb connection tubing member 264, an exhaust tubing member 265, an exhaust control valve 266, a filter 267, and a supplemental vacuum system (illustrated schematically and generally designated 250a). In this embodiment, the suction bulb 261 is a hollow sphere that may be used to produce a supply of reduced pressure for use with the treatment device 211. In addition, in some embodiments, the suction bulb 261 may also be used to receive and store exudate aspirated from the wound 215. The inlet port 262 of the suction bulb 261 is connected to one end of the bulb connection tubing member 264, which is connected to the reduced pressure supply means 240, a tubing member in this embodiment, by means of a connector 246. The connection tubing member 264 is connected to the reduced pressure supply means 240 in a manner so that the interior volume of the suction bulb 261 is in fluid communication with the volume under the cover 220 in the area of the wound 215. In this embodiment, the bulb connection tubing member 264 and the reduced pressure supply means 240 are sufficiently flexible to permit movement of the bulb connection tubing member 264 and the reduced pressure supply means 240, respectively, but are sufficiently rigid to resist constriction when reduced pressure is supplied to the cover 220 or when the location of the wound 215 is such that the patient must sit or lie upon the bulb connection tubing member 264, upon the reduced pressure supply means 240, or upon the treatment device 311. The outlet port 263 of the suction bulb 261 is connected to the exhaust tubing member 265. In this embodiment, the exhaust tubing member 265 is sufficiently flexible to permit movement of the exhaust tubing member 265, but is sufficiently rigid to resist constriction when reduced pressure is supplied to the cover 220. The inlet port 262 of the suction bulb 261 may be connected to the bulb connection tubing member 264 and the outlet port 263 of the suction bulb 261 may be connected to the exhaust tubing member 265 using any suitable means, such as by welding, fusing, adhesives, clamps, or any combination of such means. In addition, in some embodiments, which are the preferred embodiments, the suction bulb 261, the bulb connection tubing member 264, and the exhaust tubing member 265 may be fabricated as a single piece. In the illustrated embodiment, the exhaust control valve 266 and the filter 267 are operably connected to the exhaust tubing member 265. In this embodiment, the exhaust control valve 266 is used to regulate the flow of fluids (gases and liquids) to and from the suction bulb 261 and the supplemental vacuum system 250a. In embodiments of the invention that do not have a supplemental vacuum system 250a, the exhaust control valve 266 regulates flow of fluids to and from the suction bulb 261 and the outside atmosphere. Generally, the exhaust control valve 266 allows fluids to flow out of the suction bulb 261 through the outlet port 263, but not to flow in the reverse direction unless permitted by the user of the appliance 210. Any type of flow control valve may be used as the exhaust control valve 266, as long as the valve 266 is capable of operating in the anticipated environment involving reduced pressure and wound 215 exudate. Such valves are well known in the relevant art, such as sprung and unsprung flapper-type valves and disc-type valves, operating in conjunction with or without ball, gate and other similar types of valves. In this embodiment, the filter 267 is operably attached to the exhaust tubing member 265 between the outlet port 263 of the suction bulb 261 and the exhaust control valve 266. The filter 267 prevents potentially pathogenic microbes or aerosols from contaminating the exhaust control valve 266 (and supplemental vacuum system 250a), and then being vented to atmosphere. The filter 267 may be any suitable type of filter, such as a micropore filter. In other embodiments, the filter 267 may also be a hydrophobic filter that prevents any exudate from the wound 215 from contaminating the exhaust control valve 266 (and the supplemental vacuum system 250a) and then being vented to atmosphere. In still other embodiments, the filter 267 may perform both functions. It is to be noted, however, that the outlet port 263, the exhaust control valve 266, the filter 267, or any combination of the exhaust control valve 266 and the filter 267, need not be utilized in connection with the vacuum system 250 in other embodiments of the invention.

In some embodiments of the third version of the invention illustrated in FIG. 6 that do not utilize a supplemental vacuum system 250a, the suction bulb 261 may be used to produce a supply of reduced pressure in the following manner. First, the user of the appliance 210 appropriately seals all of the component parts of the appliance 210 in the manner described herein. For example, the top cup member 221 of the cover 220 is operably sealed to the interface member 222 of the cover 220, and the cover 220 is placed over and encloses the wound 215. At least a portion of the interface member 222 is sealed (or placed adjacent) to the adjacent portions 216 of the body, and the reduced pressure supply means 240 is connected to the bulb connection tubing member 264 by means of the connector 246. The user then opens the exhaust control valve 266 and applies force to the outside surface of the suction bulb 261, deforming it in a manner that causes its interior volume to be reduced. When the suction bulb 261 is deformed, the gas in the interior volume is expelled to atmosphere through the outlet port 263, the exhaust tubing member 265, the filter 267, and the exhaust control valve 266. The user then closes the exhaust control valve 266 and releases the force on the suction bulb 261. The suction bulb 261 then expands, drawing gas from the area of the wound 215 under the treatment device 211 into the suction bulb 261 and causing the pressure in such area to decrease. To release the reduced pressure, the user of the appliance 210 may open the exhaust control valve 266, allowing atmospheric air into the interior volume of the suction bulb 261. The level of reduced pressure may also be regulated by momentarily opening the exhaust control valve 266.

The suction bulb 261 may be constructed of almost any fluid impermeable flexible or semi-rigid material that is suitable for medical use and that can be readily deformed by application of pressure to the outside surface of the suction bulb 261 by users of the appliance 210 and still return to its original shape upon release of the pressure. For example, the suction bulb 261 may be constructed of rubber, neoprene, silicone, or other flexible or semi-rigid polymers, or any combination of all such materials. In addition, the suction bulb 261 may be of almost any shape, such as cubical, ellipsoidal, or polyhedral. The suction bulb 261 may also be of varying size depending upon the anticipated use of the suction bulb 261, the size of the wound treatment device 211, use of a supplemental vacuum system 250a, the level of reduced pressure desired, and the preference of the user of the appliance 210. In the embodiment of the invention illustrated in FIG. 6, the supplemental vacuum system 250a is connected to the exhaust tubing member 265 and is used to provide a supplemental supply of reduced pressure to the suction bulb 261 and treatment device 211. In this embodiment, the supplemental vacuum system 250a may have substantially the same structure, features, characteristics and operation of the various embodiments of the vacuum system 250 of the second version of the invention described above and illustrated in connection with FIG. 5. It is to be noted, however, that the supplemental vacuum system 250a need not be used in connection with the vacuum system 250 in other embodiments of the invention.

Except as illustrated and described above in connection with FIG. 6, the treatment appliance 210 may generally be used in a manner similar to the treatment appliance 110 described above and illustrated in connection with FIG. 5. As a result, except as described herein, the example of how the embodiment of the treatment appliance 110 and the cover 120 described above and illustrated in connection FIG. 5 may be used in treatment of a wound 115 also applies to the embodiment of the appliance 210 of the third version of the invention described above and illustrated in connection with FIG. 6.

What is claimed is:

1. A method of treating a wound, comprising:
positioning a membrane into contact with the wound;
positioning a wound cover over the wound, the cover having a rigid or semi-rigid ring sized to contact skin surrounding the wound so as to create a relatively fluid-tight seal;
applying reduced pressure to the wound through a port on the wound cover to draw fluid from the wound through the membrane;
while reduced pressure is being applied to the wound, collecting fluid from the wound in a space between the cover and the membrane; and
preventing the collected fluid from flowing through the port.

2. The method of claim 1, wherein a source of negative pressure positioned outside the cover applies reduced pressure to the wound.

3. The method of claim 1, wherein positioning the cover comprises positioning a rigid or semi-rigid wound cover over the wound.

4. The method of claim 1, further comprising positioning a tissue protection member adjacent the wound.

5. The method of claim 1, further comprising monitoring the volume underneath the cover.

6. The method of claim 1, comprising utilizing a filter positioned between the port and a source of reduced pressure.

7. The method of claim 1, wherein the reduced pressure is applied with a suction pump.

8. The method of claim 1, wherein the wound cover is rigid or semi-rigid and defines at least in part the space for the collected fluid.

9. A method for the treatment of a wound on a body, the method comprising:
positioning a flexible membrane in contact with the body, the flexible membrane forming a seal with the body;
placing a wound cover over the wound to enclose the wound, the wound cover forming a reversible seal with the flexible membrane; and
applying negative pressure to the wound through the wound cover and the flexible membrane;
wherein the wound cover is removable from and resealably attached to the flexible membrane while the flexible membrane remains sealed with the body.

10. The method of claim 9, further comprising:
stopping the application of negative pressure to the wound;
removing the wound cover from the flexible membrane while the flexible membrane remains sealed with the body.

11. The method of claim 9, wherein the application of negative pressure draws and collects wound exudate into a chamber between the flexible membrane and the wound cover.

12. The method of claim 11, further comprising detecting the amount of collected wound exudate.

13. The method of claim 9, wherein a gasket is positioned between the flexible membrane and the wound cover, the gasket providing a liquid-tight seal between the wound cover and the flexible membrane.

14. A method of treating a wound, comprising:
positioning a membrane into contact with the wound;
positioning a wound cover over the wound, the cover having a rigid or semi-rigid ring sized to contact skin surrounding the wound so as to create a relatively fluid-tight seal;
applying reduced pressure to the wound through a port on the wound cover to draw fluid from the wound through the membrane;
collecting fluid from the wound in a space between the cover and the membrane; and preventing the collected fluid from flowing through the port;
wherein creating a relatively fluid-tight seal comprises positioning an o-ring seal or gasket between the cover and the wound.

15. The method of claim 14, further comprising utilizing a filter to prevent collected fluid from flowing past the filter.

16. The method of claim 15, wherein the filter comprises a hydrophobic filter.

17. The method of claim 14, wherein the reduced pressure is applied with a suction pump.

18. The method of claim 14, wherein the rigid or semi-rigid ring comprises the o-ring seal or gasket.

19. The method of claim 14, further comprising positioning a tissue protection member adjacent the wound.

20. The method of claim 14, wherein the wound cover is flexible.

21. A method of treating a wound, comprising:
positioning a membrane into contact with the wound;
positioning a wound cover over the wound, the cover sized and configured to contact skin surrounding the wound so as to create a relatively fluid-tight seal;
applying reduced pressure to the wound through a port on the wound cover to draw fluid from the wound through the membrane;
collecting fluid from the wound in a chamber between the cover and the membrane;
preventing the collected fluid from flowing through the port;
removing the chamber when it is filled with wound exudate; and
subsequently positioning a second chamber between a second cover and the wound.

22. The method of claim 21, wherein the wound cover is attached to the membrane.

23. A method of treating a wound, comprising:
positioning a membrane into contact with the wound;
positioning a wound cover over the wound, the cover sized and configured to contact skin surrounding the wound so as to create a relatively fluid-tight seal;
applying reduced pressure to the wound through a port on the wound cover to draw fluid from the wound through the membrane using a source of reduced pressure;
collecting fluid from the wound in a space between the cover and the membrane; and
preventing the collected fluid from flowing through the port by using an overflow mechanism positioned at the port.

24. The method of claim 23, wherein preventing fluid from the wound from flowing through the port comprises operating a valve positioned at the port.

25. The method of claim 23, further comprising utilizing a filter to prevent collected fluid from flowing past the filter.

26. The method of claim 23, wherein the overflow mechanism comprises a flapper-type valve.

27. The method of claim 23, wherein a flow shutoff means prevents collected fluid from flowing through the port.

28. The method of claim 27, further comprising halting the application of reduced pressure when the flow shutoff means prevents collected fluid from flowing through the port.

29. The method of claim 23, wherein the membrane permits wound exudate to flow in a direction away from the wound, but does not permit wound exudate to flow in the opposite direction.

30. The method of claim 23, further comprising positioning a tissue protection member adjacent the wound.

31. A method of treating a wound, comprising:
positioning a membrane into contact with the wound;
positioning a wound cover over the wound, the cover sized and configured to contact skin surrounding the wound so as to create a relatively fluid-tight seal;
applying reduced pressure to the wound through a port on the wound cover to draw fluid from the wound through the membrane;
collecting fluid from the wound in a space between the cover and the membrane;
preventing the collected fluid from flowing through the port, and
preventing the collected fluid from flowing back through the membrane into the wound.

32. The method of claim 31, wherein the membrane permits wound exudate to flow into the space, but does not permit wound exudate to flow in the opposite direction.

33. The method of claim 31, wherein the membrane is attached to the wound cover.

34. The method of claim 33, wherein the membrane comprises one or more flow control valves.

35. The method of claim 31, further comprising utilizing a filter to prevent collected fluid from flowing past the filter.

36. The method of claim 31, wherein the membrane permits wound exudate to flow in a direction away from the wound, but does not permit wound exudate to flow in the opposite direction.

37. A method of treating a wound, comprising:
positioning a membrane into contact with the wound;
positioning a wound cover over the wound, the cover sized and configured to contact skin surrounding the wound so as to create a relatively fluid-tight seal;
applying reduced pressure to the wound to draw fluid from the wound through the membrane;
collecting fluid from the wound at a location between the membrane and the cover; and
preventing the collected fluid from flowing out of the cover while reduced pressure is being applied to the wound.

38. The method of claim 37, wherein the reduced pressure is applied from a source of negative pressure connected to the wound cover via a port on the wound cover.

39. The method of claim 38, wherein the source of negative pressure is connected to the port using a conduit.

40. The method of claim 37, further comprising monitoring the volume of collected fluid underneath the cover.

41. The method of claim 40, further comprising ceasing the application of reduced pressure once the volume of collected fluid has exceeded a predetermined limit.

42. The method of claim 37, further comprising utilizing a filter to prevent collected fluid from flowing past the filter.

43. The method of claim 42, wherein the filter comprises a hydrophobic filter.

44. The method of claim 37, wherein an overflow mechanism prevents fluid from flowing out of the cover.

45. The method of claim 37, wherein the wound cover is flexible.

46. The method of claim 37, wherein the membrane permits wound exudate to flow in a direction away from the wound, but does not permit wound exudate to flow in the opposite direction.

* * * * *

UNITED STATES PATENT AND TRADEMARK OFFICE
CERTIFICATE OF CORRECTION

PATENT NO. : 8,282,611 B2
APPLICATION NO. : 12/726161
DATED : October 9, 2012
INVENTOR(S) : Weston It is certified that error appears in the above-identified patent and that said Letters Patent is hereby corrected as shown below:

On the Title Page, item [57], Abstract, at line 17, Change "lo" to --to--.

On Title Page 5, item [56], In column 1, at line 57, Under Other Publications, change "hydrophilaand" to --hydrophila and--.

On Title Page 5, item [56], In column 1, at line 58, Under Other Publications, change "salmoncida :" to --salmonicida:--.

On Title Page 5, item [56], In column 2, at line 47, Under Other Publications, change "incuding" to --including--.

In the Specifications:

In column 2 at line 47, Change "bums," to --burns,--.
In column 8 at line 44, Change "in-the" to --in the--.
In column 14 at line 31, Change "may by" to --may be--.
In column 15 at line 41, Change "lanoline," to --lanolin,--.
In column 18 at line 11, Change "COLOPAST" to --COLOPLAST--.
In column 18 at line 12, Change "lanoline," to --lanolin,--.
In column 18 at line 13, Change "COLOPAST" to --COLOPLAST--.

Signed and Sealed this
Second Day of July, 2013

Teresa Stanek Rea
*Acting Director of the United States Patent and Trademark Office*